(12) United States Patent
Craig et al.

(10) Patent No.: US 6,465,199 B1
(45) Date of Patent: Oct. 15, 2002

(54) COMPOSITIONS AND METHODS FOR MONITORING THE MODIFICATION OF NATURAL BINDING PARTNERS

(75) Inventors: Roger K. Craig, Cheshire; John Colyer, West Yorkshire, both of (GB)

(73) Assignee: Cyclacel, Ltd., Dundee (GB)

( * ) Notice: Subject to any disclaimer, the term of this patent is extended or adjusted under 35 U.S.C. 154(b) by 0 days.

(21) Appl. No.: 09/259,478

(22) Filed: Feb. 26, 1999

(51) Int. Cl.$^7$ .................. G01N 33/573; G01N 33/53
(52) U.S. Cl. ............................ 435/7.4; 435/7.1
(58) Field of Search .................. 435/7.1, 7.4

(56) References Cited

U.S. PATENT DOCUMENTS 5,580,859 A 12/1996 Felgner et al.

FOREIGN PATENT DOCUMENTS

WO WO-9627797 A2 * 9/1996
WO WO-9844350 A1 * 10/1998

OTHER PUBLICATIONS

Arnheiter, et al., *Nature*, 294:278–280 (1981).
Atherton, et al. *J. Chem. Soc. Perkin I.*, 1981(2):538–546 (1981).
Balázs, et al., *Gene*, 40:343–348 (1985).
Banerji, et al., *Cell*, 33:729–740 (1983).
Bell, et al., *Mol. Cell. Biol.*, 16:6477–6485 (1996).
Boersma and Van Leeuwen, *J. Neurosci. Methods*, 51:217–227 (1994).
Boggs, *Int. J. Cell Cloning*, 8:80–96 (1990).
Bolivar, et al., *Gene*, 2:95–113 (1977).
Bondarenko, et al., *J. Biol. Chem.*, 272:15856–15864 (1997).
Burrows, et al., *Biochem. J.*, 324:673–680 (1997).
Carrier, et al., *J. Immunol.*, 148:1176–1181 (1992).
Cervantes–Laurean, et al., *Methods Enzymol.*, 280:275–287 (1997).
Chabalgoity, et al., *Infect. Immunol.*, 65:2402–2412 (1996).
Chang, et al., *J. Bacteriol.*, 134:1141–1156 (1978).
Chou, et al., *J. Biol. Chem.*, 270:18961–18965 (1995).
Clarke and Woodland, *Rheumatol. Rehabil.*, 14:47–49 (1975).
Coggins, et al., *J. Neurochem.*, 60:368–371 (1993).
Cox, *Methods Enzymol*, 250:105–121 (1995).
Dai, et al., *J. Biol. Chem.*, 273:3562–3573 (1998).
Davis, et al., *Science*, 253:1268–1271(1991).

(List continued on next page.)

Primary Examiner—Jon P. Weber
(74) Attorney, Agent, or Firm—Kathleen M. Williams; Palmer & Dodge, LLP

(57) ABSTRACT

This invention relates to methods and compositions for monitoring enzymatic activity as a function of the the interaction of binding partners, wherein binding is dependent upon addition or subtraction of a chemical moiety to or from one of the binding partners by a protein modifying enzyme.

9 Claims, 3 Drawing Sheets

Figure 1:
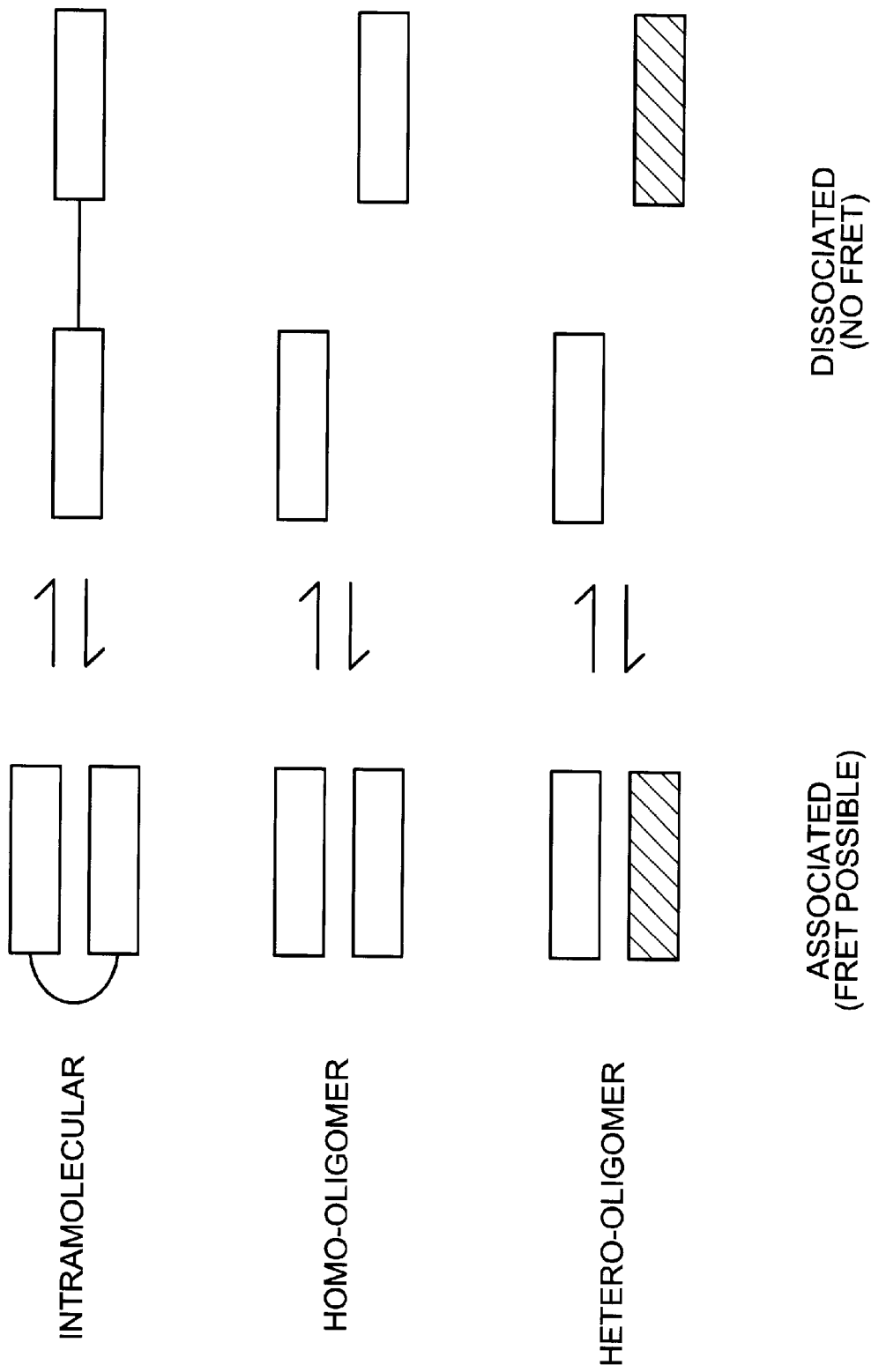

OTHER PUBLICATIONS de Murcia, et al., *Trends Cell Biol.,* 5:78–81 (1995).
Dymecki, et al., *J. Biol. Chem.,* 267:4815–4823 (1992).
Eigen and Rigler, *Proc. Natl. Acad. Sci. USA,* 91:5740–5747 (1994).
Elson and Madge, *Biopolymers,* 13:1–27 (1974).
Fox, et al., *Gene Therapy,* 3:173–178 (1996).
Garapin, et al., *Proc. Natl. Acad. Sci. USA,* 78-815–819 (1981).
Ghosh, et al., *Nature,* 373:303–310 (1995).
Gietz and Sugino, *Gene,* 74:527–534 (1988).
Gong, et al., *J. Biol. Chem.,* 272:28198–28201 (1997).
Green, et al., *Cell,* 28:477–487 (1982).
Hansen, et al., *Biochem. J.,* 308:801–813 (1995).
Hart, *Ann. Rev. Biochem.,* 66:315–335 (1997).
Haas and Siepmann, *FASEB J.,* 11:1257–1268 (1997).
Heim, et al., *Proc. Natl. Acad. Sci. USA,* 91:12501–12504 (1994).
Hengge, et al., *Nature Genet.,* 10:161–166 (1995).
Hester, et al., *Nature Structural Biology,* 2:472–479 (1005).
Hickman, et al., *Human Gene Therapy,* 5:1477–1483 (1994).
Honda, et al., *FEBS Lett.,* 420:25–27 (1997).
Horiuchi, et al., *Mol. Cell. Biol,* 12:4515–4520 (1992).
Hubbard, et al., *J. Clin. Invest.,* 84:1349–1354 (1989).
Itoh, et al., *J. Biol. Chem.,* 268:3025–3028 (1993).
Jackson, et al., *Proc. Natl. Acad. Sci. USA,* 69:2904–2909 (1972).
Jaffray, et al., *Mol. Cell. Biol.,* 15:2166–2172 (1995).
Johnson, et al., *Nature,* 346:287–291 (1990).
Johnson, et al., *Ann. Rev. Biochem.,* 63:869–914 (1994).
Johnson and Hochstrasser, *Trends Cell Biol.,* 7:408–413 (1997).
Jovin and Jovin, *Cell Structure and Function by Microspectrofluorometry,* eds. E. Kohen and J.G. Hirschberg, Academic Press (1989), Table of Contents.
Kahn, et al., *Methods Enzymol.* , 68:268–280 (1979).
Kamitani, et al., *J. Biol. Chem.,* 273:3117–3120 (1998).
Kamitani, et al., *J. Biol. Chem.,* 272:14001–14004 (1997).
Kinjo and Rigler, *Nucleic Acids Res.,* 23:1795–1799 (1995).
Kreppel, et al., *J. Biol. Chem.,* 272:9308–9315 (1997).
Levine, et al., *Comp. Biochem. Physiol.,* 72B:77–85 (1982).
Li, et al., *Cell,* 90:469–478 (1997).
Maccarrone, et al., *Biochem. Biophys. Res. Commun.,* 186:1417–1422 (1992).
Mannion–Henderson, et al., *Exp. Hematol.,* 23:1628–1632 (1995).
Mårtensson, et al., *Eur. J. Ummunol.,* 17:1499–1502 (1987).
Mátyus, *J. Photochem. Photobiol. B: Biol.,* 12:323–337 (1992).
Merrifield, *J. Am. Chem. Soc.,* 85:2149–2154 (1963).
Meyer, et al., *Gene Therapy,* 2:450–460 (1995).
Milligan, et al., *Trends Biochem. Sci.,* 20:181–186 (1995).
Minton, et al., *FEMS Microbiol. Rev.,* 17:357–364 (1995).

Müller, et al., *Nature,* 373:311–317 (1995).
Noel, et al., *Nature,* 366:654–663 (1993).
Okabe, et al., *Eur. J. Immunol.,* 22:37–43 (1992).
Okura, et al., *J. Immunol.,* 157:4277–4281 (1996).
Olszewski et al., *Nucleic Acids Res.,* 16:10765–10782 (1988).
Pan, et al., *Nature Med.,* 1:471–477 (1995).
Pawelek, et al., *Cancer Res.,* 57:4537–4544 (1997).
Perez, et al., *Plant. Mol Biol.,* 13:365–373 (1989).
Prasher, et al., *Gene,* 11:229–233 (1992).
Rarick, et al., *Science,* 256:1031–1033 (1992).
Reason, et al., *J. Biol. Chem.,* 267:16911–16921 (1992).
Resh, *Cell,* 76:411–413 (1994).
Riabowol, et al., *Cold Spring Harbor Symposia on Quantitative Biology,* 53:85–90 (1988).
Rigler, et al., *Fluorescence Spectroscopy: New Methods and Applications,* Springer Verlag, pp. 13–24 (1992).
Roussell, et al., *Mol. Gen. Genet.,* 211:202–209 (1988).
Saalbach, et al., *Mol. Gen. Genet.,* 242:226–236 (1994).
Saltzman, et al., *Cancer Biother. Radiopharm.,* 11:145–153 (1996).
Sambrook, et al., *Molecular Cloning: A Laboratory Manual,* 2nd ed., Cold Spring Harbor Laboratory Press, Cold Spring Harbor, NY (1989), Table of Contents.
Schafer, et al., *J. Immunol.,* 149:53–59 (1992).
Scott, *Microbial Reviews,* 48:1–23 (1984).
Shakin–Eshleman, *Trends in Glycoscience and Glycotechnology,* 8:115–130 (1996).
Shirataki, et al., *J. Biol. Chem.,* 266:20672–20677 (1991).
Sizemore, et al., *Science,* 270:299–302 (1995).
Spatola, in *Chemistry and Biochemistry of Amino Acids, Peptides and Proteins,* Weinstein, ed., Marcel Dekker, New York, p. 267–357 (1983).
Stryer et al., *Ann. Rev. Cell Biol.,* 2:391–419 (1986).
Sullivan, *J. Invest. Dermatol.,* 103:85S–98S (1994).
Sykes, et al., *Human Gene Ther.,* 5:837–844 (1994).
Talmadge, et al., *Proc. Natl. Acad. Sci. USA* 77:3369–3373 (1980).
Tsuboi, et al., *J. Biol. Chem.,* 269:15016–15023 (1994).
Turpen, et al., *J. Virol. Methods,* 42:227–239 (1993).
Uchida, et al., *Proc. Natl. Acad. Sci. USA,* 90:3481–3485 (1993).
Usman, et al., *Curr. Opin. Struct. Biol.,* 6:527–533 (1996).
Vile, et al., *Cancer Res.,* 53:962–967 (1993).
Wang, et al., *Nature Medicine,* 2:871–875 (1996).
Ward, et al., *Photochem. Photobiol.,* 35:803–808 (1982).
Weigert, et al., *J. Biol. Chem.,* 272:14200–14207 (1997).
Weis, et al., *Nature,* 360:127–134 (1992).
Williams, *Bone Marrow Transplant,* 5:141–144 (1990).
Wolff, J. A., et al., *Science,* 247:1465–1468 (1990).
Zolkiewska, et al., *Proc. Natl. Acad. Sci. USA,* 89:11352–11356 (1992).

\* cited by examiner

EXCIMER CONFIGURATION OF PYRENE PAIRS

```
                         SEQUENCE LISTING

<160> NUMBER OF SEQ ID NOS: 22

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: PEPTIDE
      SEQUENCE

<400> SEQUENCE: 1

Met Leu Cys Cys Met Arg Arg Thr Lys Gln Val Glu Lys Asn Asp Asp
 1               5                  10                  15

Asp

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: PEPTIDE
      SEQUENCE

<400> SEQUENCE: 2

Phe Lys Gln Arg Gln Thr Arg Gln Phe Lys
 1               5                  10

<210> SEQ ID NO 3
<211> LENGTH: 30
<212> TYPE: PRT
<213> ORGANISM: Artificial Sequence
<220> FEATURE:
<223> OTHER INFORMATION: Description of Artificial Sequence: PEPTIDE
      SEQUENCE

<400> SEQUENCE: 3

Met Phe Gln Ala Ala Glu Arg Pro Gln Glu Trp Ala Met Glu Gly Pro
 1               5                  10                  15

Arg Asp Gly Leu Lys Lys Glu Arg Leu Leu Asp Asp Arg His
            20                  25                  30

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence: PEPTIDE
      SEQUENCE

<400> SEQUENCE: 4

His Gly Ser Gly Ala Trp Leu Leu Pro Val Ser Leu Val Lys Arg Lys
 1               5                  10                  15
```

Thr Thr Leu Ala Pro
            20

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: PEPTIDE
      SEQUENCE

<400> SEQUENCE: 5

Gly Ser Ser Lys Ser Lys Pro Lys Asp
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: PEPTIDE
      SEQUENCE

<400> SEQUENCE: 6

Gly Cys Ile Lys Ser Lys Arg Lys Asp
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: PEPTIDE
      SEQUENCE

<400> SEQUENCE: 7

Gly Cys Ile Lys Ser Lys Glu Asp Lys
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: PEPTIDE
      SEQUENCE

<400> SEQUENCE: 8

Gly Cys Val Gln Cys Lys Asp Lys Glu
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: PEPTIDE
      SEQUENCE

<400> SEQUENCE: 9

Gly Cys Thr Leu Ser Ala Glu Asp Lys
1               5

<210> SEQ ID NO 10
<211> LENGTH: 9
<212> TYPE: PRT
<213> ORGANISM: Artificial Sequence
<220> FEATURE:

```
<223> OTHER INFORMATION: Description of Artificial Sequence: PEPTIDE
      SEQUENCE

<400> SEQUENCE: 10

Gly Cys Ile Lys Ser Lys Arg Lys Asp
 1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: PEPTIDE
      SEQUENCE

<400> SEQUENCE: 11

Gly Cys Val Gln Cys Lys Asp Lys Glu
 1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: PEPTIDE
      SEQUENCE

<400> SEQUENCE: 12

Gly Cys Thr Leu Ser Ala Glu Asp Lys
 1               5

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: PEPTIDE
      SEQUENCE

<400> SEQUENCE: 13

Gly Thr Thr Ser Thr Ile Gln Thr Ala Pro
 1               5                  10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: PEPTIDE
      SEQUENCE

<400> SEQUENCE: 14

Ser Ala Val Ser Ser Ala Asp Gly Thr Val Leu Lys
 1               5                  10

<210> SEQ ID NO 15
<211> LENGTH: 18
<212> TYPE: PRT
<213> ORGANISM: Artificial Sequence
<220> FEATURE:
<223> OTHER INFORMATION: Description of Artificial Sequence: PEPTIDE
      SEQUENCE

<400> SEQUENCE: 15

Asp Ser Ser Thr Asp Leu Thr Gln Thr Ser Ser Gly Thr Val Thr
 1               5                  10                  15

Leu Pro
```

```
<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: PEPTIDE
      SEQUENCE

<400> SEQUENCE: 16

Met Leu Cys Cys Met Arg Arg Thr Lys Gln Val Glu Lys Asn Asp Asp
 1               5                  10                  15

Asp

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: PEPTIDE
      SEQUENCE

<400> SEQUENCE: 17

Phe Lys Gln Arg Gln Thr Arg Gln Phe Lys
 1               5                  10

<210> SEQ ID NO 18
<211> LENGTH: 22
<212> TYPE: PRT
<213> ORGANISM: Artificial Sequence
<220> FEATURE:
<223> OTHER INFORMATION: Description of Artificial Sequence: PEPTIDE
      SEQUENCE

<400> SEQUENCE: 18

Glu Asp Ala Gly Asn Tyr Ile Lys Val Gln Phe Leu Glu Leu Asn Met
 1               5                  10                  15

Arg Arg Asp Val Lys Glu
                20

<210> SEQ ID NO 19
<211> LENGTH: 30
<212> TYPE: PRT
<213> ORGANISM: Artificial Sequence
<220> FEATURE:
<223> OTHER INFORMATION: Description of Artificial Sequence: PEPTIDE
      SEQUENCE

<400> SEQUENCE: 19

Met Phe Gln Ala Ala Glu Arg Pro Gln Glu Trp Ala Met Glu Gly Pro
 1               5                  10                  15

Arg Asp Gly Leu Lys Lys Glu Arg Leu Leu Asp Asp Arg His
            20                  25                  30

<210> SEQ ID NO 20
<211> LENGTH: 23
<212> TYPE: PRT
<213> ORGANISM: Artificial Sequence
<220> FEATURE:
<223> OTHER INFORMATION: Description of Artificial Sequence: PEPTIDE
      SEQUENCE

<400> SEQUENCE: 20

His Gly Ser Gly Ala Trp Leu Leu Pro Val Ser Leu Val Lys Arg Lys
 1               5                  10                  15
```

-continued

```
Arg Lys Thr Thr Leu Ala Pro
            20

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: PEPTIDE
      SEQUENCE

<400> SEQUENCE: 21

Met Ala Gly Gly Pro Ala Asp Thr Ser Asp Pro Leu
 1               5                  10

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: PEPTIDE
      SEQUENCE

<400> SEQUENCE: 22

Ala Gln Thr Ile Thr Ser Glu Thr Pro Ser Ser Thr Thr
 1               5                  10
```

COMPOSITIONS AND METHODS FOR MONITORING THE MODIFICATION OF NATURAL BINDING PARTNERS

FIELD OF THE INVENTION

The invention relates to monitoring of the post-translational modification of a protein.

BACKGROUND OF THE INVENTION

The post-translational modification of proteins have been known for over 40 years and since then has become a ubiquitous feature of protein structure. The addition of biochemical groups to translated polypeptides has wide-ranging effects on protein stability, protein secondary/tertiary structure, enzyme activity and in more general terms on the regulated homeostasis of cells. Such modifications include, but are not limited to, the addition of a carbohydrate (glycosylation), ADP-ribosyl (ADP ribosylation), fatty acid (prenylation, which includes but is not limited to: myrisoylation and palmitylation), ubiquitin (ubiquitination) and sentrin (sentrinization; a ubiquitination-like protein modification). Additional examples of post-translational modification include methylation, actylation, hydroxylation, iodination and flavin linkage. Many of the identified modifications have important consequences for the activity of those polypeptides so modified.

Currently there are several approaches to analyzing the state of modification of target proteins in vivo:

1. In vivo labelling of cellular substrate pools with radioactive substrate or substrate precursor molecules to result in incorporation of labeled (for example, radiolabeled) moieties (e.g., fatty acyl (including, but not limited to, myristoyl and palmityl) sentrin, methyl, actyl, hydroxyl, iodine, flavin, ubiquitin or ADP-ribosyls), which are added to target proteins. Analysis of modified proteins is typically performed by electrophoresis and autoradiography, with specificity enhanced by immunoprecipitation of proteins of interest prior to electrophoresis.

2. Back-labeling. The enzymatic incorporation of a labeled (including, but not limited to, with a radioactive and fluorescent label) moiety into a protein in vitro to estimate the state of modification in vivo.

3. Detection of alteration in electrophoretic mobility of modified protein compared with unmodified (e.g., glycosylated or ubiquitinated) protein.

4. Thin-layer chromatography of radiolabelled fatty acids extracted from the protein of interest.

5. Partitioning of protein into detergent-rich or detergent-poor layer by phase separation, and the effects of enzyme treatment of the protein of interest on the partitioning between aqueous and detergent-rich environments.

6. The use of cell-membrane-permeable protein-modifying enzyme inhibitors (e.g., Wortmannin, staurosporine) to block modification of target proteins and comparable inhibitors of the enzymes involved in other forms of protein modification (above).

7. Antibody recognition of the modified form of the protein (e.g., using an antibody directed at ubiquitin or carbohydrate epitopes), e.g., by Western blotting, of either 1- or 2-dimensional gels bearing test protein samples.

8. Lectin-protein interaction in Western blot format as an assay of the presence of particular carbohydrate groups (defined by the specificity of the lectin in use).

9. The exploitation of eukaryotic microbial systems to identify mutations in protein-modifying enzymes.

These strategies have certain limitations. Monitoring states of modification by pulse or steady-state labelling is merely a descriptive strategy to show which proteins are modified when samples are separated by gel electrophoresis and visualized by autoradiography. This is unsatisfactory, due to the inability to identify many of the proteins that are modified. A degree of specificity is afforded to this technique if it is combined with immunoprecipitation; however, this is of course limited by the availability of antibodies to target proteins. Moreover, only highly-expressed proteins are readily detectable using this technique, which may fail to identify many low-abundance proteins, which are potentially important regulators of cellular functions.

The use of enzyme inhibitors to block activity is also problematic. For example, very few enzyme inhibitors have adequate specificity to allow for the unequivocal correlation of a given enzyme with a specific modification reaction. Indeed, many inhibitors have a broad inhibitory range. This is clearly unsatisfactory because more than one biochemical pathway may be affected during treatment making the assignment of the effects almost impossible.

Finally, yeast (*Saccharomyces cervisiae* and *Schizosaccharomyces pombe*) has been exploited as a model organism for the identification of gene function using recessive mutations. It is through research on the effects of these mutations that the functional specificities of many protein-modifying enzymes have been elucidated. However, these molecular genetic techniques are not easily transferable to higher eukaryotes, which are diploid and therefore not as genetically tractable as these lower eukaryotes.

A non-limiting example of post-translational modification is provided by the Ras proteins, which are a conserved group of polypeptides located at the plasma membrane which exist in either a GTP-bound active state or in a GDP-bound inactive state. This family of proteins operates in signal transduction pathways that regulate cell growth and differentiation. In higher eukaryotes, Ras is a key regulator that mediates signal transduction from cell surface tyrosine kinase receptors to the nucleus via activation of the MAP kinase cascade. Recent studies have demonstrated that Ras directly binds a serine/threonine kinase, Raf-1, a product of the c-raf-1 proto-oncogene, and that this association leads to stimulation of the activity of Raf-1 to phosphorylate MAP kinase kinase (MEK).

An important post-translational modification is the addition of ubiquitin to selected polypeptides. This provides a key mechanism by which to control the abundance of important regulatory proteins, for example, G1 and mitotic cyclins and the p53 tumor suppressor protein. Ubiquitin is a highly conserved 76-amino-acid cellular polypeptide. The role of ubiquitin in targeting proteins for degradation involves the specific ligation of ubiquitin to the $\epsilon$ group of lysine residues in proteins that are to be degraded or internalized from the plasma membrane. The ubiquitin tag determines the fate of the protein and results in its selective proteolysis. Recently a number of factors have been isolated and shown to be involved in the ubiquitination process.

The initial step in the addition of ubiquitin to a protein is the activation of ubiquitin by the ubiquitin activating enzyme, E1. This is an ATP-dependent step resulting in the formation of a thioester bond between the carboxyl terminal glycine of ubiquitin and the active site cysteine residue of E1. Activated ubiquitin then interacts with a second factor, the E2 protein. A thioester bond forms between the activated glycine residue of ubiquitin and a cysteine residue in a specific E2 protein. The E2 proteins represent a family of closely-related proteins encoded by different genes that confer specificity in the proteolytic process. The ligation of ubiquitin to target proteins is effected by the involvement of a further factor, a ubiquitin ligase, E3, of which a number are known (in yeast, reviewed by Haas and Siepmann, 1997, *FASEB J.*, 11: 1257–1268; in humans, see Honda et al., 1997, *FEBS Lett.*, 420: 25–27). E3 completes the final step of ubiquitination by attaching ubiquitin via the ε amino group on lysine residues in proteins to be targeted for degradation. Moreover, E3 is able to add ubiquitin to ubiquitin molecules already attached to target proteins, thereby resulting in polyubiquitinated proteins that are ultimately degraded by the multi-subunit proteasome.

An example of heterodimer association is described in patent application number WO92/00388. It describes an adenosine 3:5 cyclic monophosphate (cAMP) dependent protein kinase which is a four-subunit enzyme being composed of two catalytic polypeptides (C) and two regulatory polypeptides (R). In nature the polypeptides associate in a stoichiometry of $R_2C_2$. In the absence of cAMP the R and C subunits associate and the enzyme complex is inactive. In the presence of cAMP the R subunit functions as a ligand for cAMP resulting in dissociation of the complex and the release of active protein kinase. The invention described in WO92/00388 exploits this association by adding fluorochromes to the R and C subunits.

The polypeptides are labeled (or 'tagged') with fluorophores having different excitation/emission wavelengths. The emission from one such fluorophore following excitation effects a second excitation/emission event in the second fluorophore. By monitoring the fluorescence emission of each fluorophore, which reflects the presence or absence of fluorescence energy transfer between the two, it is possible to derive the concentration of cAMP as a function of the level of association between the R and C subunits. Therefore, the natural affinity of the C subunit for the R subunit has been exploited to monitor the concentration of a specific metabolite, namely cAMP.

The prior art teaches that intact, fluorophore-labeled proteins can function as reporter molecules for monitoring the formation of multi-subunit complexes from protein monomers; however, in each case, the technique relies on the natural ability of the protein monomers to associate.

Tsien et al. (WO97/28261) teach that fluorescent proteins having the proper emission and excitation spectra that are brought into physically close proximity with one another can exhibit fluorescence resonance energy transfer ("FRET"). The invention of WO97/28261 takes advantage of that discovery to provide tandem fluorescent protein constructs in which two fluorescent protein moieties capable of exhibiting FRET are coupled through a linker to form a tandem construct. In the assays of the Tsien et al. application, protease activity is monitored using FRET to determine the distance between fluorophores controlled by a peptide linker and subsequent hydrolysis thereof. Other applications rely on a change in the intrinsic fluorescence of the protein as in the kinase assays of WO98/06737.

The present invention instead encompasses the use of FRET or other detection procedures to monitor the association of polypeptides, as described herein, which are labeled with fluorescent labels (protein and chemical); in the invention, FRET, fluorescence correlation spectroscopy, fluorescence anisotropy, monomer:excimer fluorescence or other techniques indicate the proximity of two labeled polypeptide binding partners, which labeled partners associate either in the presence or absence of a given post-translational modification to an site which is present in the natural binding domain and, optionally, in the binding partner, but not into the fluorophore, reflecting the modification state of one or both of the binding partners and, consequently, the level of activity of a protein-modifying enzyme. The invention further provides methods which employ non-fluorescent labels including, but not limited to, radioactive labels. In addition, the invention encompasses methods which do not employ detectable labels; such methods include, but are not limited to, the detection of the inhibition or reconstition of enzymatic activity, which inhibition or reconstitution results from modification-dependent binding or dissociation between a natural binding domain and a binding partner therefor.

There is a need in the art for efficient means of monitoring and/or modulating post-translational protein modification. Further, there is a need to develop a technique whereby the addition/removal of a modifying group can be monitored continuously during real time to provide a dynamic assay system that also has the ability to resolve spatial information.

SUMMARY OF THE INVENTION

The invention provides natural binding domains, sequences and polypeptides, all as defined below, as well as kits comprising these molecules and assays of enzymatic function in which they are employed as reporter molecules.

One aspect of the invention is an isolated natural binding domain and a binding partner therefor, wherein the isolated natural binding domain includes a site for post-translational modification and binds the binding partner therefor in a manner dependent upon modification of the site.

The invention additionally encompasses a method for monitoring activity of an enzyme comprising performing a detection step to detect binding of an isolated natural binding domain and a binding partner therefor as a result of contacting one or both of the isolated natural binding domain and the binding partner with the enzyme, wherein the isolated natural binding domain includes a site for post-translational modification and binds the binding partner in a manner dependent upon modification of the site and wherein detection of binding of the isolated natural binding domain and the binding partner as a result of the contacting is indicative of enzyme activity.

Another aspect of the invention is a method for monitoring activity of an enzyme comprising performing a detection step to detect dissociation of an isolated natural binding domain from a binding partner therefor as a result of contacting one or both of the isolated natural binding domain and the binding partner with said enzyme, wherein the isolated natural binding domain includes a site for post-translational modification and binds the binding partner in a manner dependent upon modification of the site and wherein detection of dissociation of the isolated natural binding domain from the binding partner as a result of the contacting is indicative of enzyme activity.

As used herein, the term "binding domain" in a three-dimensional sense refers to the amino acid residues of a first polypeptide required for modification-dependent binding between the first polypeptide and its binding partner. The amino acids of a "binding domain" may be either contiguous or non-contiguous and may form a binding pocket for modification-dependent binding. A binding domain must include at least 1 amino acid, and may include 2 or more, preferably 4 or more, amino acids which are contiguous or non-contiguous, but are necessary for modification-dependent binding to the binding partner, and may include a full-length protein.

A binding domain which is of use in the invention is a "natural binding domain" (i.e., a binding domain that exhibits modification-dependent binding to a binding partner in nature). A natural binding domain of use in the invention may be isolated or may be present in the context of a larger polypeptide molecule (i.e., one which comprises amino acids other than those of the natural binding domain), which molecule may be either naturally-occurring or recombinant and, in the case of the latter, may comprise either natural or non-natural amino acid sequences outside the binding domain.

As used herein with regard to modification of a polypeptide, the terms "site" and "site sufficient for the addition of" refer to an amino acid sequence which is recognized by (i.e., a signal for) a modifying enzyme for the purpose of post-translational modification (i.e., addition or removal of a "moiety" as defined below) of the polypeptide or a portion thereof. A "site" additionally refers to the single amino acid which is modified. It is contemplated that a site comprises a small number of amino acids, as few as one but typically from 2 to 10, less often up to 30 amino acids, and further that a site comprises fewer than the total number of amino acids present in the polypeptide.

In an enzymatic assay of the invention, a "site", for post-translational modification may be present on either or both of a natural binding domain and its binding partner. If such sites are present on both the natural binding domain and the binding partner, binding between the natural binding domain and its binding partner may be dependent upon the modification state of either one or both sites. If a single polypeptide chain comprises the natural binding domain and its binding partner (or two natural binding domains), the state of post-translational modification of one or both sites will determine whether binding between the two domains occurs.

As used herein, the term "modification" or "post-translational modification" refers to the addition or removal of a chemical "moiety", as described herein, to/from a site on a polypeptide chain and does not refer to other post-translational events which do not involve addition or removal of such a moiety as described herein, and thus does not include simple cleavage of the reporter molecule polypeptide backbone by hydrolysis of a peptide bond, but does include hydrolysis of an isopeptide bond (e.g., in the removal of ubiquitin).

As used interchangeably herein, the terms "moiety" and "group" refer to one of the post-translationally added or removed groups referred to herein: i.e., one of a ubiquitin moiety, a glycosyl moiety, a fatty acyl moiety, a sentrin moiety or an ADP-ribosyl moiety. A "moiety" or "group" as defined herein does not refer to a phosphate.

As used herein, the term "binding partner" refers to a polypeptide or fragment thereof (a peptide) that binds to a binding domain, sequence or polypeptide, as defined herein, in a manner which is dependent upon the state of modification of a site for post-translational modification which is, at a minimum, present upon the binding domain, sequence or polypeptide; the binding partner itself may, optionally, comprise such a site and binding between the binding domain, fragment or polypeptide with its corresponding binding partner may, optionally, depend upon modification of that site. A binding partner does not necessarily have to contain a site for post-translational modification if such a site is not required to be present on it for modification-dependent association between it and a binding domain, sequence or polypeptide. Binding partners of use in the invention are those which are found in nature and exhibit natural modification-dependent binding to a natural binding domain, sequence or polypeptide of the invention as defined herein. In one embodiment of the invention, a binding partner is shorter (i.e., by at least one N-terminal or C-terminal amino acid) than the natural full-length polypeptide.

As used herein, the term "associates" or "binds" refers to a natural binding domain as described herein and its binding partner having a binding constant sufficiently strong to allow detection of binding by FRET or other detection means, which are in physical contact with each other and have a dissociation constant (Kd) of about 10 $\mu$M or lower. The contact region may include all or parts of the two molecules. Therefore, the terms "substantially dissociated" and "dissociated" or "substantially unbound" or "unbound" refer to the absence or loss of contact between such regions, such that the binding constant is reduced by an amount which produces a discernable change in a signal compared to the bound state, including a total absence or loss of contact, such that the proteins are completely separated, as well as a partial absence or loss of contact, so that the body of the proteins are no longer in close proximity to each other but may still be tethered together or otherwise loosely attached, and thus have a dissociation constant greater than 10 $\mu$M (Kd). In many cases, the Kd will be in the mM range. The terms "complex", "dimer", "multimer" and "oligomer" as used herein, refer to the natural binding domain and its binding partner in the associated or bound state. More than one molecule of each of the two or more proteins may be present in a complex, dimer, multimer or oligomer according to the methods of the invention.

As used herein in reference to a natural binding domain or other polypeptide, the term "isolated" refers to a molecule or population of molecules that is substantially pure (i.e., free of contaminating molecules of unlike amino acid sequence).

As used herein in reference to the purity of a molecule or population thereof, the term "substantially" refers to that which is at least 50%, preferably 60–75%, more preferably from 80–95% and, most preferably, from 98–100% pure.

"Naturally-occurring" as used herein, as applied to a polypeptide or polynucleotide, refers to the fact that the polypeptide or polynucleotide can be found in nature. One such example is a polypeptide or polynucleotide sequence that is present in an organism (including a virus) that can be isolated form a source in nature.

The term "synthetic", as used herein, is defined as any amino- or nucleic acid sequence which is produced via chemical synthesis.

In an assay of the invention, post-translational modification is reversible, such that a repeating cycles of addition and removal of a modifying moiety may be observed, although such cycles may not occur in a living cell found in nature.

An advantage of assays of the invention is that they may, if desired, be performed in "real time". As used herein in reference to monitoring, measurements or observations in assays of the invention, the term "real time" refers to that which is performed contemporaneously with the monitored, measured or observed events and which yields a result of the monitoring, measurement or observation to one who performs it simultaneously, or effectively so, with the occurrence of a monitored, measured or observed event. Thus, a "real time" assay or measurement contains not only the measured and quantitated result, such as fluorescence, but expresses this in real time, that is, in hours, minutes, seconds, milliseconds, nanoseconds, picoseconds, etc. Shorter times exceed the instrumentation capability; further, resolution is also limited by the folding and binding kinetics of polypeptides.

As used herein, the term "binding sequence" refers to that portion of a polypeptide comprising at least 1 amino acid, preferably at least 2, more preferably at least 4, and up to 8, 10, 100 or 1000 contiguous (i.e., covalently linked by peptide bonds) amino acid residues or even as many residues as are comprised by a full-length protein, that are sufficient for modification-dependent binding to a binding partner. A binding sequence may exist on a polypeptide molecule that consists solely of binding sequence amino acid residues or may, instead, be found in the context of a larger polypeptide chain (i.e., one that comprises amino acids other than those of the binding sequence).

As used herein in reference to those binding sequences that are of use in the invention, the term "natural binding sequence" refers to a binding sequence, as defined above, which consists of an amino acid sequence which is found in nature and which is naturally dependent upon the modification state of a site for post-translational modification found within it for binding to a binding partner. A "natural binding sequence" may be present either in isolation or in the context of a larger polypeptide molecule, which molecule may be naturally-occurring or recombinant. If present, amino acids outside of the binding sequence may be either natural, i.e., from the same polypeptide sequence from which the fragment is derived, or non-natural, i.e., from another (different) polypeptide, or non-natural (a sequence that is not derived from any known polypeptide). In assays of the invention, a binding sequence and its binding partner may exist either on two different polypeptide chains or on a single polypeptide chain.

As used herein, the term "binding polypeptide" refers to a molecule comprising multiple binding sequences, as defined above, which sequences are derived from a single, naturally-occurring polypeptide molecule and are both necessary and, in combination, sufficient to permit modification-state-dependent binding of the binding polypeptide to its binding partner, as defined above, wherein the sequences of the binding polypeptide are either contiguous or are non-contiguous. As used herein in reference to the component binding sequences of a binding polypeptide, the term "non-contiguous" refers to binding sequences which are linked by intervening naturally-occurring, as defined herein, or non-natural amino acid sequences or other chemical or biological linker molecules such are known in the art. The amino acids of a polypeptide that do not significantly contribute to the modification-state-dependent binding of that polypeptide to its binding partner may be those amino acids which are naturally present and link the binding sequences in a binding polypeptide or they may be derived from a different natural polypeptide or may be wholly non-natural. In assays of the invention, a binding polypeptide and its binding partner (which may, itself, be a binding domain, sequence or polypeptide, as defined herein) may exist on two different polypeptide chains or on a single polypeptide chain.

As used herein, the terms "polypeptide" and "peptide" refer to a polymer in which the monomers are amino acids and are joined together through peptide or disulfide bonds. The terms subunit and domain also may refer to polypeptides and peptides having biological function. A peptide useful in the invention will at least have a binding capability, i.e, with respect to binding as- or to a binding partner, and also may have another biological function that is a biological function of a protein or domain from which the peptide sequence is derived. "Polypeptide" refers to a naturally-occurring amino acid chain comprising a subset of the amino acids of a full-length protein, wherein the subset comprises at least one fewer amino acid than does the full-length protein, or a "fragment thereof" or "peptide", such as a selected region of the polypeptide that is of interest in a binding assay and for which a binding partner is known or determinable. "Fragment thereof" thus refers to an amino acid sequence that is a portion of a full-length polypeptide, between about 8 and about 1000 amino acids in length, preferably about 8 to about 300, more preferably about 8 to about 200 amino acids, and even more preferably about 10 to about 50 or 100 amino acids in length. "Peptide" refers to a short amino acid sequence that is 10–40 amino acids long, preferably 10–35 amino acids. Additionally, unnatural amino acids, for example, β-alanine, phenyl glycine and homoarginine may be included. Commonly-encountered amino acids which are not gene-encoded may also be used in the present invention. All of the amino acids used in the present invention may be either the D- or L-optical isomer. The L-isomers are preferred. In addition, other peptidomimetics are also useful, e.g. in linker sequences of polypeptides of the present invention (see Spatola, 1983, in *Chemistry and Biochemistry of Amino Acids, Peptides and Proteins*, Weinstein, ed., Marcel Dekker, New York, p. 267).

As used herein, the terms "protein", "subunit" and "domain" refer to a linear sequence of amino acids which exhibits biological function. This linear sequence includes full-length amino acid sequences (e.g. those encoded by a full-length gene or polynucleotide), or a portion or fragment thereof, provided the biological function is maintained by that portion or fragment. The terms "subunit" and "domain" also may refer to polypeptides and peptides having biological function. A peptide useful in the invention will at least have a binding capability, i.e, with respect to binding as or to a binding partner, and also may have another biological function that is a biological function of a protein or domain from which the peptide sequence is derived.

"Polynucleotide" refers to a polymeric form of nucleotides of at least 10 bases in length and up to 1,000 bases or even more, either ribonucleotides or deoxyribonucleotides or a modified form of either type of nucleotide. The term includes single and double stranded forms of DNA.

It is preferred in an isolated natural binding domain and binding partner therefor that the site comprises a sequence which directs modification by one or more of the following enzymes: a carbohydrate transferase (e.g., a UDP-N-Acetylglucosamine-Dolichyl-phosphate-N-acetylsglucosamine phosphotransferase or an O-GlcNAc transferase), a ubiquitin activating enzyme E1, a ubiquitin conjugating enzyme E2, a ubiquitin conjugating enzyme Ubc9, a ubiquitin protein ligase E3, a poly (ADP-ribose) polymerase, a fatty acyl transferase (e.g., a peptide N-myristoyltransferase) and an NAD:Arginine ADP ribosyltransferase. The site does not comprise a sequence which directs modification by a protein kinase or phosphatase.

It is additionally preferred that the site permits addition of a chemical moiety which may be: a ubiquitin moiety, a glycosyl moiety, an ADP-ribosyl moiety, a fatty acid moiety and a sentrin moiety, and the addition prevents binding of the isolated natural binding domain to the binding partner.

As used herein the term "prevents binding" or "prevents association" refers to the ability of at least one of a ubiquitin moiety, a glycosyl moiety, a fatty acyl moiety, a sentrin moiety or an ADP-ribosyl moiety to inhibit the association, as defined above, of an isolated natural binding domain and a binding partner thereof by at least 10%, preferably by 25–50%, highly preferably by 75–90% and, most preferably, by 95–100% relative the association observed in the absence of such a modification under the same experimental conditions.

According to another preferred embodiment, the site permits addition of a chemical moiety which may be: a ubiquitin moiety, a glycosyl moiety, an ADP-ribosyl moiety, a fatty acid moiety and a sentrin moiety, and the addition promotes binding of the isolated natural binding domain to the binding partner.

As used herein, the term "promotes binding" refers to that which causes an increase in binding of the natural binding domain and its binding partner of at least two-fold, preferably 10- to 20-fold, highly preferably 50- to 100-fold, more preferably from 200- to 1000-fold, and, most preferably, from 200 to 10,000-fold.

Preferably, the site permits removal of a chemical moiety which may be: a ubiquitin moiety, a glycosyl moiety, an ADP-ribosyl moiety, a fatty acid moiety and a sentrin moiety, and the removal prevents binding of the isolated natural binding domain to the binding partner.

It is preferred that the site permits removal of a chemical moiety which may be: a ubiquitin moiety, a glycosyl moiety, an ADP-ribosyl moiety, a fatty acid moiety and a sentrin moiety, and the removal promotes binding of the isolated natural binding domain to the binding partner.

Preferably, at least one of the isolated natural binding domain and the binding partner comprises a detectable label, more preferably, the detectable label emits light and, most preferably, the light is fluorescent.

A "fluorescent tag", "fluorescent label" or "fluorescent group" refers to either a fluorophore or a fluorescent protein or fluorescent fragment thereof. "Fluorescent protein" refers to any protein which fluoresces when excited with appropriate electromagnetic radiation. This includes proteins whose amino acid sequences are either natural or engineered. A "fluorescent protein" is a full-length fluorescent protein or fluorescent fragment thereof. By the same token, the term "linker" refers to the radical of a molecular linker that is coupled to both the donor and acceptor protein molecules, such as an amino acid sequence joining two natural binding domains, sequences or polypeptides or joining a natural binding domain, sequence or polypeptide and its corresponding binding partner, or a disulfide bond between two polypeptide sequences, whether the sequences are present on the same- or on different polypeptide chains.

It is contemplated that with regard to fluorescent labels employed in FRET, the reporter labels are chosen such that the emission wavelength spectrum of one (the "donor") is within the excitation wavelength spectrum of the other (the "acceptor"). With regard to a fluorescent label and a quencher employed in a single-label detection procedure in an assay of the invention, it is additionally contemplated that the fluorophore and quencher are chosen such that the emission wavelength spectrum of the fluorophore is within the absorption spectrum of the quencher, such that when the fluorophore and the quencher with which it is employed are brought into close proximity by binding of the natural binding domain, sequence or polypeptide upon which one is present with the binding partner comprising the other, detection of the fluorescent signal emitted by the fluorophore is reduced by at least 10%, preferably 20–50%, more preferably 70–90% and, most preferably, by 95–100%. A typical quencher reduces detection of a fluorescent signal by approximately 80%.

According to one preferred embodiment, one of the isolated natural binding domain and the binding partner comprises a quencher for the detectable label.

The invention additionally provides a kit comprising an isolated natural binding domain and a binding partner therefor, wherein the isolated natural binding domain includes a site for post-translational modification and binds the binding partner in a manner dependent upon modification of the site, and packaging materials therefor.

It is preferred that the kit further comprises a buffer which permits modification-dependent binding of the isolated natural binding domain and the binding partner.

As used herein, the term "buffer" refers to a medium which permits activity of the protein-modifying enzyme used in an assay of the invention, and is typically a low-ionic-strength buffer or other biocompatible solution (e.g., water, containing one or more of physiological salt, such as simple saline, and/or a weak buffer, such as Tris or phosphate, or others as described hereinbelow), a cell culture medium, of which many are known in the art, or a whole or fractionated cell lysate. Such a buffer permits dimerization of a non-ubiquitinated and/or non-prenylated and/or non-sentrinated and/or non-ADP-ribosylated and/or non-glycosylated natural binding domain of the invention and a binding partner therefor and, preferably, inhibits degradation and maintains biological activity of the reaction components. Inhibitors of degradation, such as protease inhibitors (e.g., pepstatin, leupeptin, etc.) and nuclease inhibitors (e.g., DEPC) are well known in the art. Lastly, an appropriate buffer may comprise a stabilizing substance such as glycerol, sucrose or polyethylene glycol.

As used herein, the term "physiological buffer" refers to a liquid medium that mimics the salt balance and pH of the cytoplasm of a cell or of the extracellular milieu, such that post-translational protein modification reactions and protein:protein binding are permitted to occur in the buffer as they would in vivo.

Preferably, the buffer additionally permits modification of the site for protein modification by one or more of the following enzymes: a carbohydrate transferase (e.g., a UDP-N-Acetylglucosamine-Dolichyl-phosphate-N-acetylsglucosamine phosphotransferase or an O-GlcNAc transferase), a ubiquitin activating enzyme E1, a ubiquitin conjugating enzyme E2, a ubiquitin conjugating enzyme Ubc9, a ubiquitin protein ligase E3, a poly (ADP-ribose) polymerase, a fatty acyl transferase (e.g., a peptide N-myristoyltransferase) and an NAD:Arginine ADP ribosyltransferase.

It is preferred that the kit further comprises one or more of the following enzymes: carbohydrate transferase (e.g., a UDP-N-Acetylglucosamine-Dolichyl-phosphate-N-acetylsglucosamine phosphotransferase or an O-GlcNAc transferase), a ubiquitin activating enzyme E1, a ubiquitin conjugating enzyme E2, a ubiquitin conjugating enzyme Ubc9, a ubiquitin protein ligase E3, a poly (ADP-ribose) polymerase, a fatty acyl transferase (e.g., a peptide N-myristoyltransferase) and an NAD:Arginine ADP ribosyltransferase.

It is additionally preferred that the kit further comprises a substrate for the enzyme which may be: ubiquitin, sentrin, nicotinamide adenine dinucleotide ($NAD^+$), uridine-diphosphate-N-acetylglucosamine-dolichyl-phosphate (UDP-N-acetylglucosamine-dolichyl-phosphate), palmytyl CoA, myristoyl CoA and UDP-N-acetylglucosamine.

It is contemplated that at least a part of a substrate of an enzyme of use in the invention is transferred to an modification site on an isolated natural binding domain of the invention. As used herein, the term "at least a part of a substrate" refers to a portion (e.g., a fragment of an amino acid sequence, a moiety or a group, as defined above) which comprises less than the whole of the substrate for the enzyme, the transfer of which portion to a modification site on an isolated natural binding domain and, optionally, to a site on a binding partner therefor, both as defined above, is catalyzed by the enzyme.

Preferably, the kit further comprises a cofactor for said enzyme.

It is preferred that at least one of the isolated natural binding domain and the binding partner comprises a detectable label, more preferred that the detectable label emits light and most preferred that the light is fluorescent.

An enzyme of use in the invention may be natural or recombinant or, alternatively, may be chemically synthesized. If either natural or recombinant, it may be substantially pure (i.e., present in a population of molecules in which it is at least 50% homogeneous), partially purified (i.e., represented by at least 1% of the molecules present in a fraction of a cellular lysate) or may be present in a crude biological sample.

As used herein, the term "sample" refers to a collection of inorganic, organic or biochemical molecules which is either found in nature (e.g., in a biological- or other specimen) or in an artificially-constructed grouping, such as agents which might be found and/or mixed in a laboratory. Such a sample may be either heterogeneous or homogeneous.

As used herein, the interchangeable terms "biological specimen" and "biological sample" refer to a whole organism or a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). "Biological sample" and "biological specimen" further refer to a homogenate, lysate or extract prepared from a whole organism or a subset of its tissues, cells or component parts, or a fraction or portion thereof. Lastly, "biological sample" refers to a medium, such as a nutrient broth or gel in which an organism has been propagated, which contains cellular components, such as proteins or nucleic acid molecules.

As used herein, the term "organism" refers to all cellular life-forms, such as prokaryotes and eukaryotes, as well as non-cellular, nucleic acid-containing entities, such as bacteriophage and viruses.

In a method as described above, it is preferred that at least one of the isolated natural binding domain and the binding partner is labeled with a detectable label, more preferred that the label emits light and most preferred that the light is fluorescent.

Preferably, the detection step is to detect a change in signal emission by the detectable label.

According to one preferred embodiment, the method further comprises exciting the detectable label and monitoring fluorescence emission.

Preferably, the enzyme is one of the following enzymes: a carbohydrate transferase (e.g., a UDP-N-Acetylglucosamine-Dolichyl-phosphate-N-acetylsglucosamine phosphotransferase or an O-GlcNAc transferase), a ubiquitin activating enzyme E1, a ubiquitin conjugating enzyme E2, a ubiquitin conjugating enzyme Ubc9, a ubiquitin protein ligase E3, a poly (ADP-ribose) polymerase, a fatty acyl transferase (e.g., a peptide N-myristoyltransferase) and an NAD:Arginine ADP ribosyltransferase. The enzyme is not a protein kinase or phosphatase.

It is preferred that the method further comprises the step, prior to or after the detection step, of contacting the isolated natural binding domain and the binding partner with an agent which modulates the activity of the enzyme.

As used herein with regard to a biological or chemical agent, the term "modulate" refers to enhancing or inhibiting the activity of a protein-modifying enzyme in an assay of the invention; such modulation may be direct (e.g. including, but not limited to, cleavage of—or competitive binding of another substance to the enzyme) or indirect (e.g. by blocking the initial production or, if required, activation of the modifying enzyme).

"Modulation" refers to the capacity to either increase or decease a measurable functional property of biological activity or process (e.g., enzyme activity or receptor binding) by at least 10%, 15%, 20%, 25%, 50%, 100% or more; such increase or decrease may be contingent on the occurrence of a specific event, such as activation of a signal transduction pathway, and/or may be manifest only in particular cell types.

The term "modulator" refers to a chemical compound (naturally occurring or non-naturally occurring), such as a biological macromolecule (e.g., nucleic acid, protein, non-peptide, or organic molecule), or an extract made from biological materials such as bacteria, plants, fungi, or animal (particularly mammalian) cells or tissues, or even an inorganic element or molecule. Modulators are evaluated for potential activity as inhibitors or activators (directly or indirectly) of a biological process or processes (e.g., agonist, partial antagonist, partial agonist, antagonist, antineoplastic agents, cytotoxic agents, inhibitors of neoplastic transformation or cell proliferation, cell proliferation-promoting agents, and the like) by inclusion in screening assays described herein. The activities (or activity) of a modulator may be known, unknown or partially-known. Such modulators can be screened using the methods described herein.

The term "candidate modulator" refers to a compound to be tested by one or more screening method(s) of the invention as a putative modulator. Usually, various predetermined concentrations are used for screening such as 0.01 $\mu$M, 0.1 $\mu$M, 1.0 $\mu$M, and 10.0 $\mu$M, as described more fully hereinbelow. Test compound controls can include the measurement of a signal in the absence of the test compound or comparison to a compound known to modulate the target.

The invention also provides a method of screening for a candidate modulator of enzymatic activity of one or more of the following enzymes: a carbohydrate transferase (e.g., a UDP-N-Acetylglucosamine-Dolichyl-phosphate-N-acetylsglucosamine phosphotransferase or an O-GlcNAc transferase), a ubiquitin activating enzyme E1, a ubiquitin conjugating enzyme E2, a ubiquitin conjugating enzyme Ubc9, a ubiquitin protein ligase E3, a poly (ADP-ribose) polymerase, a fatty acyl transferase (e.g, a peptide N-myristoyltransferase) and an NAD:Arginine ADP ribosyltransferase, the method comprising contacting an isolated natural binding domain, a binding partner therefor and an enzyme with a candidate modulator of the enzyme, wherein the natural binding domain includes a site for post-translational modification and binds the binding partner in a manner that is dependent upon modification of the site by the enzyme and wherein at least one of the isolated natural binding domain and the binding partner comprises a detectable label, and monitoring the binding of the isolated natural binding domain to the binding partner, wherein binding or dissociation of the isolated natural binding domain and the binding partner as a result of the contacting is indicative of modulation of enzymatic activity by the candidate modulator of the enzyme.

It is preferred that the detectable label emits light and highly preferred that the light is fluorescent.

Preferably, the monitoring comprises measuring a change in energy transfer between a label present on the isolated natural binding domain and a label present on the binding partner.

A final aspect of the invention is a method of screening for a candidate modulator of enzymatic activity of one or more of the following enzymes: a carbohydrate transferase (e.g., a UDP-N-Acetylglucosamine-Dolichyl-phosphate-N-acetylsglucosamine phosphotransferase or an O-GlcNAc transferase), a ubiquitin activating enzyme E1, a ubiquitin conjugating enzyme E2, a ubiquitin conjugating enzyme Ubc9, a ubiquitin protein ligase E3, a poly (ADP-ribose) polymerase, a fatty acyl transferase (e.g., a peptide N-myristoyltransferase) and an NAD:Arginine ADP ribosyltransferase, the method comprising contacting an assay system with a candidate modulator of enzymatic activity of such an enzyme, and monitoring binding of an isolated natural binding domain and a binding partner therefor in the assay system, wherein the natural binding domain includes a site for post-translational modification and binds the binding partner in a manner that is dependent upon modification of the site by at least one such enzyme in the assay system, wherein at least one of the isolated natural binding domain and the binding partner comprises a detectable label, and wherein binding or dissociation of the isolated natural binding domain and the binding partner as a result of the contacting is indicative of modulation of enzymatic activity by the candidate modulator of such an enzyme.

In a particularly preferred embodiment, in one of the methods described above, the method comprises real-time observation of association of an isolated natural binding domain and its binding partner.

Further features and advantages of the invention will become more fully apparent in the following description of the embodiments and drawings thereof, and from the claims.

BRIEF DESCRIPTIONS OF THE DRAWINGS

FIG. 1 diagrams double- and single-chain enzymatic assay formats of the invention.

Figure 2:
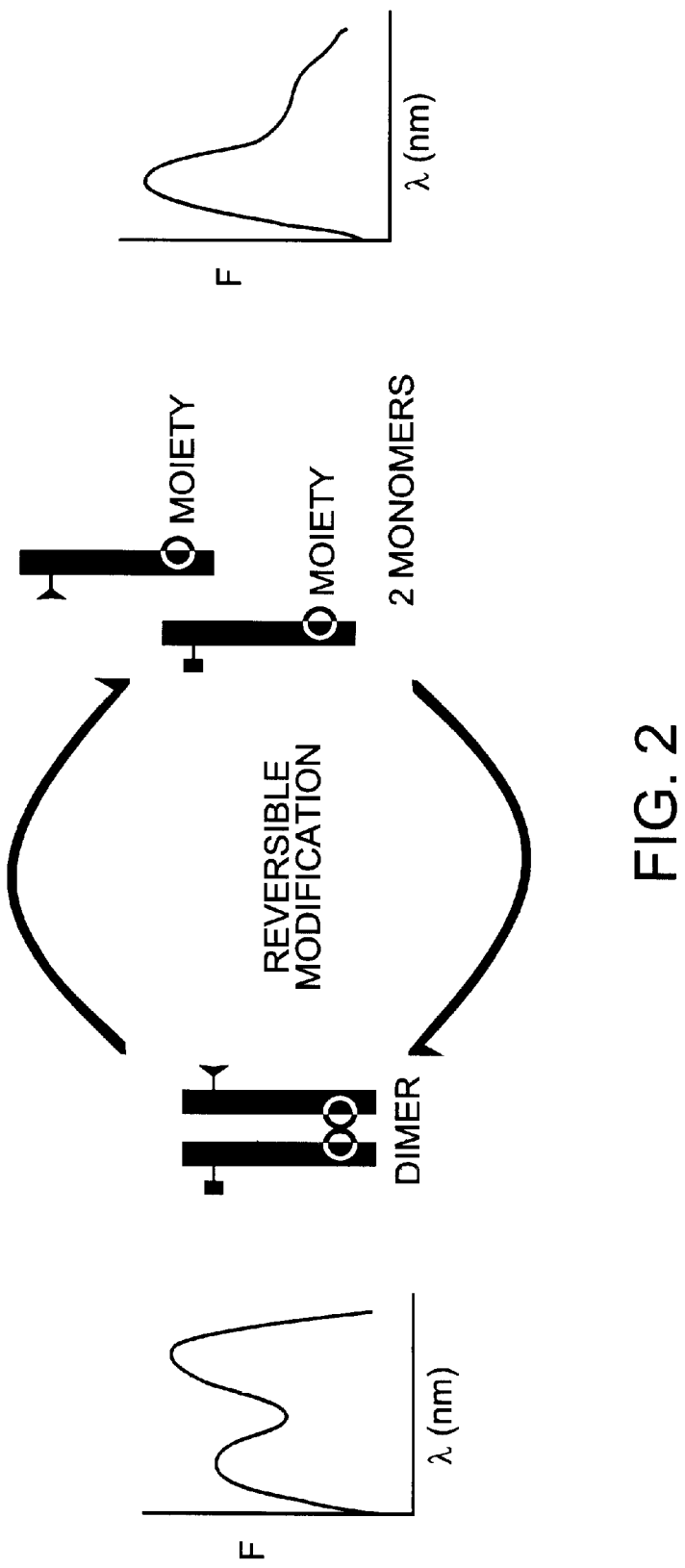

FIG. 2 presents a schematic overview of FRET in an assay of the invention.

Figure 3:
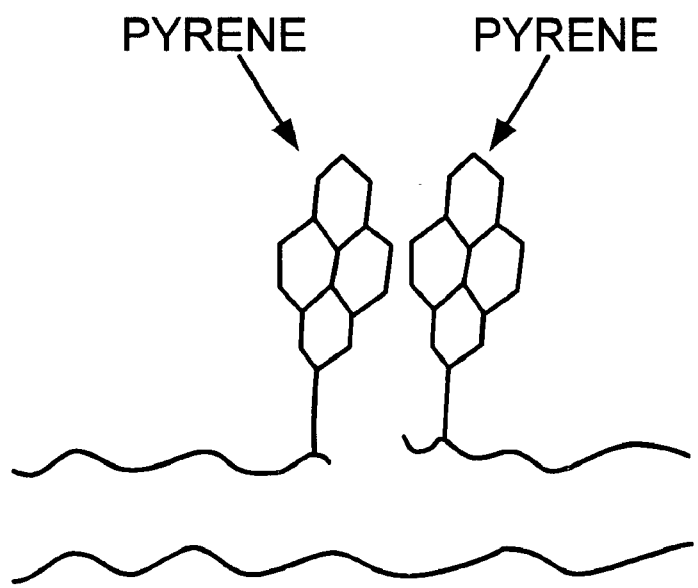

FIG. 3 presents monomer:excimer fluorescence.

DESCRIPTION

The invention is based upon the discovery that a natural binding domain, sequence or polypeptide, as defined above, associates with a binding partner to form a complex or dissociates from a binding partner, in a manner that is dependent upon the presence or absence of a chemical moiety, and that is detectable and measurable in a highly sensitive manner that may be observed in real time.

A. Natural Binding Domains of Use in the Invention and Binding Partners Therefor The invention provides reporter molecules and assays for measuring the activity of protein modifying enzymes. These reporter molecules are naturally-occurring polypeptides which include natural binding domains, natural binding sequences and natural binding polypeptides, each as defined above, which are used in assays of the invention in combination with polypeptide binding partners, also as defined above.

By monitoring the association or dissociation of a natural binding domain, sequence or polypeptide and its binding partner in the presence of a known or candidate protein modifying enzyme, the activity of such an enzyme can be measured. In such assays, one or both of the natural binding domain, sequence or polypeptide and its binding partner comprises a detectable label including, but not exclusively, a fluorescent or other light-emitting label, which may be either chemical or proteinaceous. By measuring changes in signal emission before and after addition to the mixture comprising the natural binding domain, sequence or polypeptide and its binding partner of the enzyme to be assayed, the extent of modification can be calculated. An important feature of the invention is that such measurements (e.g., of a shift in FRET or other signal emitted by a detectable label) can be performed in real-time. This allows for sensitive assessment of enzyme reaction kinetics based upon the rate of change of the protein-binding-dependent signal emission or absorption by the label(s).

Assays in which the above reporter molecules are used according to the invention may be performed either in double- or single-chain format (FIG. 1). In double-chain format, natural binding domain, sequence or polypeptide is comprised by a different polypeptide chain from that comprising or consisting of the binding partner and is not otherwise covalently linked to it. In single-chain format, the natural binding domain, sequence or polypeptide is covalently linked to its binding partner, either through an intervening amino acid sequence or a chemical linker.

The binding partner of a natural binding domain, sequence or polypeptide may, itself, be a natural binding domain, sequence or polypeptide as defined herein. If so, binding of the two molecules may depend upon the modification state of one or both in a manner that is comparable to that found in nature.

Methods by which assays of the invention are performed are described in detail in the following sections.

Unless defined otherwise, all technical and scientific terms used herein have the same meaning as commonly understood by one of ordinary skill in the art (e.g, in cell culture, molecular genetics, nucleic acid chemistry, hybridization techniques and biochemistry). Standard techniques are used for molecular, genetic and biochemical methods (see generally, Sambrook et al., *Molecular Cloning: A Laboratory Manual,* 2d ed (1989) Cold Spring Harbor Laboratory Press, Cold Spring Harbor, N.Y., which is incorporated herein by reference), chemical methods, pharmaceutical formulation and delivery and treatment of patients.

B. Methods by Which to Detect Protein:Protein Binding in Assays of the Invention According to the invention, the activity of a modifying enzyme is assayed by measuring the formation or destruction of protein:protein complexes when the modifying enzyme is present with a natural binding domain and its corresponding binding partner under conditions which permit modifying activity. Methods which enable the detection of protein:protein complexes (i.e., methods which allow one of skill in the art to discriminate between polypeptide pairing partners which are bound and those which are unbound) are known in the art. Of particular use in the invention are those methods which entail fluorescent labelling of the natural binding domain and/or its binding partner, and subsequent detection of changes in fluorescence, whether in frequency or level, following incubation of the labeled assay components with the candidate modifying enzyme. Several such procedures are briefly summarized below.

Fluorescent Resonance Energy Transfer (FRET)

A tool with which to assess the distance between one molecule and another (whether protein or nucleic acid) or between two positions on the same molecule is provided by the technique of fluorescent resonance energy transfer (FRET), which is now widely known in the art (for a review, see Matyus, 1992, *J. Photochem. Photobiol, B: Biol.,* 12: 323–337, which is herein incorporated by reference). FRET is a radiationless process in which energy is transferred from an excited donor molecule to an acceptor molecule; the efficiency of this transfer is dependent upon the distance between the donor and acceptor molecules, as described below. Since the rate of energy transfer is inversely proportional to the sixth power of the distance between the donor and acceptor, the energy transfer efficiency is extremely sensitive to distance changes. Energy transfer is said to occur with detectable efficiency in the 1–10 nm distance range, but is typically 4–6 nm for favorable pairs of donor and acceptor.

Radiationless energy transfer is based on the biophysical properties of fluorophores. These principles are reviewed elsewhere (Lakowicz, 1983, *Principles of Fluorescence Spectroscopy,* Plenum Press, New York; Jovin and Jovin, 1989, *Cell Structure and Function by Microspectrofluorometry,* eds. E. Kohen and J. G. Hirschberg, Academic Press, both of which are incorporated herein by reference). Briefly, a fluorophore absorbs light energy at a characteristic wavelength. This wavelength is also known as the excitation wavelength. The energy absorbed by a flurochrome is subsequently released through various pathways, one being emission of photons to produce fluorescence. The wavelength of light being emitted is known as the emission wavelength and is an inherent characteristic of a particular fluorophore. Radiationless energy transfer is the quantum-mechanical process by which the energy of the excited state of one fluorophore is transferred without actual photon emission to a second fluorophore. That energy may then be subsequently released at the emission wavelength of the second fluorophore. The first fluorophore is generally termed the donor (D) and has an excited state of higher energy than that of the second fluorophore, termed the acceptor (A). The essential features of the process are that the emission specturm of the donor overlap with the excitation spectrum of the acceptor, and that the donor and acceptor be sufficiently close. The distance over which radiationless energy transfer is effective depends on many factors including the fluorescence quantum efficiency of the donor, the extinction coefficient of the acceptor, the degree of overlap of their respective spectra, the refractive index of the medium, and the relative orientation of the transition moments of the two fluorophores. In addition to having an optimum emission range overlapping the excitation wavelength of the other fluorophore, the distance between D and A must be sufficiently small to allow the radiationless transfer of energy between the fluorophores.

FRET may be performed either in vivo or in vitro. Proteins are labeled either in vivo or in vitro by methods known in the art. According to the invention, a natural binding domain, sequence or polypeptide and its binding partner, comprised either by the same or by different polypeptide molecules, are differentially labeled, one with a donor and the other with an acceptor, and differences in fluorescence between a test assay, comprising a protein modifying enzyme, and a control, in which the modifying enzyme is absent, are measured using a fluorimeter or laser-scanning microscope. It will be apparent to those skilled in the art that excitation/detection means can be augmented by the incorporation of photomultiplier means to enhance detection sensitivity. The differential labels may comprise either two different fluorescent labels (e.g., fluorescent proteins as described below or the fluorophores rhodamine, fluorescein, SPQ, and others as are known in the art) or a fluorescent label and a molecule known to quench its signal; differences in the proximity of the natural binding domain to its binding partner with- and without the protein-modifying enzyme can be gauged based upon a difference in the fluorescence spectrum or intensity observed.

This combination of protein-labeling methods and devices confers a distinct advantage over prior art methods for determining the activity of protein-modifying enzymes, as described above, in that results of all measurements are observed in real time (i.e., as a reaction progresses). This is significantly advantageous, as it allows both for rapid data collection and yields information regarding reaction kinetics under various conditions.

A sample, whether in vitro or in vivo, assayed according to the invention therefore comprises a mixture at equilibrium of the labeled natural binding domain and its binding partner which, when disassociated from one another, fluoresce at one frequency and, when complexed together, fluoresce at another frequency or, alternatively, of molecules which either do or do not fluoresce depending upon whether or not they are associated.

The natural binding domain and/or binding partner therefor is modified to allow the attachment of a fluorescent label to the surface of that molecule or is fused in-frame with a fluorescent protein, as described below. The choice of fluorescent label will be such that upon excitation with light, labeled peptides which are associated will show optimal energy transfer between fluorophores. In the presence of a protein modifying enzyme that recognizes the site for protein modification present on the natural binding domain and, optionally, the binding partner, the natural binding domain and its binding partner dissociate due to a structural or electrostatic change which occurs as a consequence of addition or removal of a chemical moiety, as described herein, to/from the enzyme recognition site, thereby leading to a decrease in energy transfer and increased emission of light by the donor fluorophore. In this way, the state of polypeptide modification can be monitored and quantitated in real-time. This scheme, which represents the broadest embodiment of the invention, is shown in FIG. 2.

As used herein, the terms "fluorophore" and "fluorochrome" refer interchangeably to a molecule which is capable of absorbing energy at a wavelength range and releasing energy at a wavelength range other than the absorbance range. The term "excitation wavelength" refers to the range of wavelengths at which a fluorophore absorbs energy. The term "emission wavelength" refers to the range of wavelength that the fluorophore releases energy or fluoresces.

A non-limiting list of chemical fluorophores of use in the invention, along with their excitation and emission wavelengths, is presented in Table 1.

TABLE 1

| Fluorophore | Excitation (nm) | Emission (nm) | Color |
|---|---|---|---|
| PKH2 | 490 | 504 | green |
| PKH67 | 490 | 502 | green |
| Fluorescein (FITC) | 495 | 525 | green |
| Hoechst 33258 | 360 | 470 | blue |
| R-Phycoerythrin (PE) | 488 | 578 | orange-red |
| Rhodamine (TRITC) | 552 | 570 | red |
| Quantum Red ™ | 488 | 670 | red |
| PKH26 | 551 | 567 | red |
| Texas Red | 596 | 620 | red |
| Cy3 | 552 | 570 | red |

Examples of fluorescent proteins which vary among themselves in excitation and emission maxima are listed in Table 1 of WO 97/28261 (Tsien et al., 1997, supra). These (each followed by [excitation max./emission max.] wavelengths expressed in nanometers) include wild-type Green Fluorescent Protein [395(475)/508] and the cloned mutant of Green Fluorescent Protein variants P4 [383/447], P4-3 [381/445], W7 [433(453)/475(501)], W2 [432(453)/480], S65T [489/511], P4-1 [504(396)/480], S65A [471/504], S65C [479/507], S65L [484/510], Y66F [360/442], Y66W [458/480], I0c [513/527], W1B [432(453)/476(503)], Emerald [487/508] and Sapphire [395/511]. This list is not exhaustive of fluorescent proteins known in the art; additional examples are found in the Genbank and SwissProt public databases.

A number of parameters of fluorescence output are envisaged including
1) measuring fluoresence emitted at the emission wavelength of the acceptor (A) and donor (D) and determining the extent of energy transfer by the ratio of their emission amplitudes;
2) measuring the fluoresence lifetime of D;
3) measuring the rate of photobleaching of D;
4) measuring the anisotropy of D and/or A; or
5) measuring the Stokes shift monomer; excimer fluorescence.

Certain of these techniques are presented below.

Alternative Fluorescent Techniques Suitable for Monitoring Protein:Protein Binding in Assays of the Invention One embodiment of the technology can utilize monomer:excimer fluorescence as the output. The association of a natural binding domain with a binding partner in this format is shown in FIG. 3.

The fluorophore pyrene when present as a single copy displays fluorescent emission of a particular wavelength significantly shorter than when two copies of pyrene form a planar dimer (excimer), as depicted. As above, excitation at a single wavelength (probably 340 nm) is used to review the excimer fluorescence (~470 nm) over monomer fluorescence (~375 nm) to quantify assembly:disassembly of the reporter molecule.

Additional embodiments of the present invention are not dependent on FRET. For example the invention can make use of fluorescence correlation spectroscopy (FCS), which relies on the measurement of the rate of diffusion of a label (see Elson and Magde, 1974 *Biopolymers*, 13: 1–27; Rigler et al., 1992, in *Fuorescence Spectroscopy: New Methods and Applications*, Springer Verlag, pp.13–24; Eigen and Rigler, 1994, Proc. Natl. Acad. Sci. U.S.A., 91: 5740–5747; Kinjo and Rigler, 1995, *Nucleic Acids Res.*, 23: 1795–1799).

In FCS, a focused laser beam illuminates a very small volume of solution, of the order of $10^{-15}$ liter, which at any given point in time contains only one molecule of the many under analysis. The diffusion of single molecules through the illuminated volume, over time, results in bursts of fluorescent light as the labels of the molecules are excited by the laser. Each individual burst, resulting from a single molecule, can be registered.

A labeled polypeptide will diffuse at a slower rate if it is large than if it is small. Thus, multimerized polypeptides will display slow diffusion rates, resulting in a lower number of fluorescent bursts in any given timeframe, while labeled polypeptides which are not multimerized or which have dissociated from a multimer will diffuse more rapidly. Binding of polypeptides according to the invention can be calculated directly from the diffusion rates through the illuminated volume.

Where FCS is employed, rather than FRET, it is not necessary to label more than one polypeptide. Preferably, a single polypeptide member of the multimer is labeled. The labeled polypeptide dissociates from the multimer as a result of modification, thus altering the FCS reading for the fluorescent label.

A further detection technique which may be employed in the method of the present invention is the measurement of time-dependent decay of fluorescence anisotropy. This is described, for example, in Lacowicz, 1983, *Principles of Fluorescence Spectroscopy*, Plenum Press, New York, incorporated herein by reference (see, for example, page 167).

Fluorescence anisotropy relies on the measurement of the rotation of fluorescent groups. Larger multimers of polypeptides rotate more slowly than monomers, allowing the formation of multimers to be monitored.

Non-fluorescent Methods to Detect Protein:Protein Binding According to the Invention The invention may be configured to exploit a number of non-fluorescent labels. In a first embodiment, the natural binding domain and binding partner therefor form, when bound, an active enzyme which is capable of participating in an enzyme-substrate reaction which has a detectable endpoint. The enzyme may comprise two or more polypeptide chains or regions of a single chain, such that upon binding of the natural binding domain to the binding partner, which are present either on two different polypeptide chains or in two different regions of a single polypeptide, these components assemble to form a functional enzyme. Enzyme function may be assessed by a number of methods, including scintillation counting and photospectroscopy. In a further embodiment, the invention may be configured such that the label is a redox enzyme, for example glucose oxidase, and the signal generated by the label is an electrical signal Modification of the natural binding domain and, optionally, its binding partner according to the invention is required to inhibit binding and, consequently, enzyme component assembly, thus reducing enzyme activity.

In another assay format, an enzyme is used together with a modulator of enzyme activity, such as an inhibitor or a cofactor. In such an assay, one of the enzyme and the inhibitor or cofactor is an natural binding domain, the other its binding partner. Binding of the enzyme to its inhibitor or cofactor results in modulation of enzymatic activity, which is detectable by conventional means (such as monitoring for the conversion of substrate to product for a given enzyme).

Fluorescent Protein Labels in Assays of the Invention

In a FRET assay of the invention, the fluorescent protein labels are chosen such that the excitation spectrum of one of the labels (the acceptor label) overlaps with the emission spectrum of the excited fluorescent label (the donor label). The donor label is excited by light of appropriate intensity within the donor's excitation spectrum. The donor then emits some of the absorbed energy as fluorescent light and dissipates some of the energy by FRET to the acceptor fluorescent label. The fluorescent energy it produces is quenched by the acceptor fluorescent label. FRET can be manifested as a reduction in the intensity of the fluorescent signal from the donor, reduction in the lifetime of its excited state, and re-emission of fluorescent light at the longer wavelengths (lower energies) characteristic of the acceptor. When the donor and acceptor labels become spatially separated, FRET is diminished or eliminated.

One can take advantage of the FRET exhibited by a natural binding domain and its binding partner labeled with different fluorescent protein labels, wherein one is linked to a donor and the other to an acceptor label, in monitoring protein modification according to the present invention. A single polypeptide may comprises a blue fluorescent protein donor label and a green fluorescent protein acceptor label, wherein each is fused to a different assay component (i.e., in which one is fused to the natural binding domain and the other to its binding partner); such a construct is herein referred to as a "tandem" fusion protein. Alternatively, two distinct polypeptides ("single" fusion proteins) one comprising or a natural binding domain and the other its binding partner may be differentially labeled with the donor and acceptor fluorescent protein labels, respectively. The construction and use of tandem fusion proteins in the invention can reduce significantly the molar concentration of peptides necessary to effect an association between differentially-labeled polypeptide assay components relative to that required when single fusion proteins are instead used. The labeled natural binding domain, sequence or polypeptide and/or its binding partner may be produced via the expression of recombinant nucleic acid molecules comprising an in-frame fusion of sequences encoding a such a polypeptide and a fluorescent protein label either in vitro (e.g., using a cell-free transcription/translation system, as described below, or instead using cultured cells transformed or transfected using methods well known in the art) or in vivo, for example in a transgenic animal including, but not limited to, insects, amphibians and mammals. A recombinant nucleic acid molecule of use in the invention may be constructed and expressed by molecular methods well known in the art, and may additionally comprise sequences including, but not limited to, those which encode a tag (e.g., a histidine tag) to enable easy purification, a secretion signal, a nuclear localization signal or other primary sequence signal capable of targeting the construct to a particular cellular location, if it is so desired.

The means by which a natural binding domain and its binding partner are assayed for association using fluorescent protein labels according to the invention may be briefly summarized as follows:

Whether or not the natural binding domain and its binding partner are present on a single polypeptide molecule, one is labeled with a green fluorescent protein, while the other is preferably labeled with a red or, alternatively, a blue fluorescent protein. Useful donor:acceptor pairs of fluorescent proteins (see Tsien et al., 1997, supra) include, but are not limited to:

Donor: S72A, K79R, Y145F, M153A and T203I (excitation λ395 nm; emission λ511)
Acceptor: S65G, S72A, K79R and T203Y (excitation λ514 nm; emission λ527 nm), or
T203Y/S65G, V68L, Q69K or S72A (excitation λ515 nm; emission λ527 nm).

An example of a blue:green pairing is P4-3 (shown in Table 1 of Tsien et al., 1997, supra) as the donor label and S65C (also of Table 1 of Tsien et al., 1997, supra) as the acceptor label. The natural binding domain, sequence or polypeptide and corresponding binding partner are exposed to light at, for example, 368 nm, a wavelength that is near the excitation maximum of P4-3. This wavelength excites S65C only minimally. Upon excitation, some portion of the energy absorbed by the blue fluorescent protein label is transferred to the acceptor label through FRET if the natural binding domain, sequence or polypeptide and its binding partner are in close association. As a result of this quenching, the blue fluorescent light emitted by the blue fluorescent protein is less bright than would be expected if the blue fluorescent protein existed in isolation. The acceptor label (S65C) may re-emit the energy at longer wavelength, in this case, green fluorescent light.

After modification of one or both of the natural binding domain and its binding partner by a protein modifying enzyme, the natural binding domain and its binding partner (and, hence, the green and red or, less preferably, green and blue fluorescent proteins) physically separate or associate, accordingly inhibiting or promoting FRET. For example, if activity of the modifying enzyme results in dissociation of a protein:protein complex, the intensity of visible blue fluorescent light emitted by the blue fluorescent protein increases, while the intensity of visible green light emitted by the green fluorescent protein as a result of FRET, decreases.

Such a system is useful to monitor the activity of enzymes that modify a site for post-translational modification of a natural binding domain and, optionally, its binding partner to which the fluorescent protein labels are fused as well as the activity of protein modifying enzymes or candidate modulators thereof.

In particular, this invention contemplates assays in which the amount- or activity of a modifying enzyme in a sample is determined by contacting the sample with a natural binding domain and its binding partner, differentially-labeled with fluorescent proteins, as described above, and measuring changes in fluorescence of the donor label, the acceptor label or the relative fluorescence of both. Fusion proteins, as described above, which comprise either one or both of the labeled natural binding domain and its binding partner of an assay of the invention can be used for, among other things, monitoring the activity of a protein modifying enzyme inside the cell that expresses the recombinant tandem construct or two different recombinant constructs.

Advantages of single- and tandem fluorescent protein/polypeptides comprising a natural binding domain fused to a fluorescent protein include the greater extinction coefficient and quantum yield of many of these proteins compared with those of the Edans fluorophore. The acceptor in such a construct or pair of constructs is, itself, a fluorophore rather than a non-fluorescent quencher like Dabcyl. Alternatively, in single-label assays of the invention, whether involving use of a chemical fluorophore or a single fluorescent fusion construct, such a non-fluorescent quencher may be used. Thus, the enzyme's substrate (i.e., the natural binding domain and, optionally, the corresponding binding partner), and reaction products (i.e., the natural binding domain and, optionally, the corresponding binding partner after modification) are both fluorescent but with different fluorescent characteristics.

In particular, the substrate and modified products exhibit different ratios between the amount of light emitted by the donor and acceptor labels. Therefore, the ratio between the two fluorescences measures the degree of conversion of substrate to products, independent of the absolute amount of either, the optical thickness of the sample, the brightness of the excitation lamp, the sensitivity of the detector, etc. Furthermore, Aequorea-derived or -related fluorescent protein labels tend to be protease resistant. Therefore, they are likely to retain their fluorescent properties throughout the course of an experiment.

Reporter Polypeptide Fusion Construct According to the Invention

As stated above, recombinant nucleic acid constructs of particular use in the invention are those which comprise in-frame fusions of sequences encoding a natural binding domain or a binding partner therefor and a fluorescent protein. If a natural binding domain and its binding partner are to be expressed as part of a single polypeptide, the nucleic acid molecule additionally encodes, at a minimum, a donor fluorescent protein label fused to one, an acceptor fluorescent protein label fused to the other, a linker that couples the two and is of sufficient length and flexibility to allow for folding of the polypeptide and pairing of the natural binding domain, sequence or polypeptide with the binding partner, and gene regulatory sequences operatively linked to the fusion coding sequence. If single fusion proteins are instead encoded (whether by one or more nucleic acid molecules), each nucleic acid molecule need only encode a natural binding domain or a binding partner therefor, fused either to a donor or acceptor fluorescent protein label and operatively linked to gene regulatory sequences.

"Operatively-linked" refers to polynucleotide sequences which are necessary to effect the expression of coding and non-coding sequences to which they are ligated. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, components whose presence can influence expression, and can also include additional components whose presence is advantageous, for example, leader sequences and fusion partner sequences.

As described above, the donor fluorescent protein label is capable of absorbing a photon and transferring energy to another fluorescent label. The acceptor fluorescent protein label is capable of absorbing energy and emitting a photon. If needed, the linker connects the natural binding domain and its binding partner either directly or indirectly, through an intermediary linkage with one or both of the donor and acceptor fluorescent protein labels. Regardless of the relative order of the natural binding domain, its binding partner and the donor and acceptor fluorescent protein labels on a polypeptide molecule, it is essential that sufficient distance be placed between the donor and acceptor by the linker and/or the natural binding domain and its binding partner to ensure that FRET does not occur unless the natural binding domain and its binding partner bind. It is desirable, as described in greater detail in WO97/28261, to select a donor fluorescent protein label with an emission spectrum that overlaps with the excitation spectrum of an acceptor fluorescent protein label. In some embodiments of the invention the overlap in emission and excitation spectra will facilitate FRET. A fluorescent protein of use in the invention includes, in addition to those with intrinsic fluorescent properties, proteins that fluoresce due intramolecular rearrangements or the addition of cofactors that promote fluorescence.

For example, green fluorescent proteins ("GFPs") of cnidarians, which act as their energy-transfer acceptors in bioluminescence, can be used in the invention. A green fluorescent protein, as used herein, is a protein that fluoresces green light, and a blue fluorescent protein is a protein that fluoresces blue light. GFPs have been isolated from the Pacific Northwest jellyfish, *Aequorea victoria*, from the sea pansy, *Renilla reniformis*, and from *Phialidium gregarium*. (Ward et al., 1982, *Photochem, Photobiol.*, 35: 803–808; Levine et al., 1982, *Comp. Biochem. Physiol.*, 72B: 77–85).

A variety of Aequorea-related GFPs having useful excitation and emission spectra have been engineered by modifying the amino acid sequence of a naturally occurring GFP from *Aequorea victoria*. (Prasher et al., 1992, Gene, 111: 229–233; Heim et al., 1994, *Proc. Natl. Acad. Sci. U.S.A.*, 91: 12501–12504; PCT/US95/14692). As used herein, a fluorescent protein is an Aequorea-related fluorescent protein if any contiguous sequence of 150 amino acids of the fluorescent protein has at least 85% sequence identity with an amino acid sequence, either contiguous or non-contiguous, from the wild-type Aequorea green fluorescent protein (SwissProt Accession No. P42212). More preferably, a fluorescent protein is an Aequorea-related fluorescent protein if any contiguous sequence of 200 amino acids of the fluorescent protein has at least 95% sequence identity with an amino acid sequence, either contiguous or non-contiguous, from the wild type Aequorea green fluorescent protein of SwissProt Accession No. P42212. Similarly, the fluorescent protein may be related to Renilla or Phialidium wild-type fluorescent proteins using the same standards.

Aequorea-related fluorescent proteins include, for example, wild-type (native) *Aequorea victoria* GFP, whose nucleotide and deduced amino acid sequences are presented in Genbank Accession Nos. L29345, M62654, M62653 and others Aequorea-related engineered versions of Green Fluorescent Protein, of which some are listed above. Several of these, i.e., P4, P4-3, W7 and W2 fluoresce at a distinctly shorter wavelength than wild type.

Recombinant nucleic acid molecules encoding single- or tandem fluorescent protein/polypeptide comprising a natural binding domain and/or a binding partner therefor fused to a fluorescent protein useful in the invention may be expressed either for in vivo assay of the activity of a modifying enzyme on the encoded products. Alternatively, the encoded fusion proteins may be isolated prior to assay, and instead assayed in a cell-free in vitro assay system, as described elsewhere herein.

C. Protein Modifications in Assays of the Invention

The invention provides reagents and methods for assaying the activity of enzymes which perform post-translational modification of proteins. Table 2 lists non-limiting examples of post-translational modifications.

| Modification | Protein Source | Consensus Sequence/ Sequence | SEQ ID NO: | Reference/ Genbank No. |
|---|---|---|---|---|
| | | Modified residues indicated in bold. Residues forming part of the recognition site are shown in italics. | | |
| ADP-Ribosylation | B-50 | ¹MLCCMRRTKQVEKND DD | SEQ ID NO: 1 | Coggins et al., 1993, J. Neurochem., 60: 368–71 |
| | γ subunit of cGMP phosphodiesterase | ³⁰FKQRQTRQFK | SEQ ID NO: 2 | X04270 |
| Ubiquitination | IκB | ¹MFQAAERPQEWA MEG PRDGLKKERLLDD RH | SEQ ID NO: 3 | M69043 |
| | β-Galactosidase | ¹HGSGAWLLPVSL VKR KTTLAP | SEQ ID NO: 4 | Johnson et al., 1990, Nature, 346: 287–291 |
| N-Myristoylation | Src | ¹GSSKSKPKD | SEQ ID NO: 5 | Resh, 1994, Cell, 76: 411–413 |
| | Lyn | 1 GCIKSKRKD | SEQ ID NO: 6 | Resh, 1994, supra |
| | Yes | 1 GCIKSKEDK | SEQ ID NO: 7 | Resh, 1994, supra |
| | Fyn | 1 GCVQCKDKF | SEQ ID NO: 8 | Resh, 1994, supra |
| | Gα | 1 GCTLSAEDK | SEQ ID NO: 9 | Resh, 1994, supra |
| Palmitylation | Lyn | 1 GCIKSKRKD | SEQ ID NO: 10 | M64608 |
| | Fyn | 1 GCVQCKDKE | SEQ ID NO: 11 | M14676 |
| | Gαi2 | 1 GCTLSAEDK | SEQ ID NO: 12 | Milligan et al., 1995, Trends Biochem. Sci., 20: 181–186 |
| N-Glycosylation | | -NXS/T- X can be any amino acid except P | | Shakineshleman, 1996, Trends in Glycoscience and Glycotechnology, 8: 115–130 |
| O-Glycosylation | p67$^{SRF}$ | ²⁷⁴GTTSTIQTAP ³¹³SAVSSADGTVLK ³⁷⁴DSSTDLTQTSSS GTVTLP | SEQ ID NO: 13 SEQ ID NO: 14 SEQ ID NO: 15 | J03161 |
| Sentrinization | RanGAP1 | | | Johnson and Hochstrasser, 1997, Trends Cell. Biol., 7: 408–413 |
| | PML | | | Kamitani et al., 1998, J. Biol. Chem., 273: 3117–3120 |

A simple FRET assay based upon these modifications to site for post-translational modification present on a natural binding domain may be performed as presented below. It is contemplated that other light-based detection assays, such as those involving single labels, labels and corresponding quenchers, etc. can be employed.

(F1-NBD)(F2-partner) + substrate ⟶ F1-M-NBD + F2-partner + byproduct where:
NBD=natural binding domain
M=modification
F1=donor fluorophore
F2=acceptor fluorophore Alternatively, a FRET-based assay may follow a format such as:

F1-NBD + F2-partner + substrate ⟶ (No FRET)

(F1-M-NBD)(F2-partner) + byproduct (FRET)

Table 3 provides a non-limiting list of enzymes that are representative of the classes of modifying enzymes discussed herein as being amenable to assay according to the invention.

TABLE 3

| Modification | Enzyme | Specific Action | GenBank No./ Reference |
|---|---|---|---|
| Mono-ADP-Ribosylation | AND:ArginineADP-ribosyl transferase | | Zolkiewska et al., 1992, PNAS B2: 11352-6 |
| Poly-ADP-Ribosylation | Drosophila PARP | | D13806, D13807, D13808 |
| Ubiquitination | E1 E2(UBC8) E3(RSP5) | Ubiquitination of large subunit of RNA pol II (Rpb 1) (NB, E2 and E3 confer substrate specificity on the ubiquitination) | X55386, X56507, M65083, U18916, L11119, L11120, U00092, U75972 |
| N-Myristoylation | Glycylpeptide-N-tetradecanoyltransferase (peptide N-myristoyltransferase) | | M86707 |
| N-Glycosylation | UDP-N-acetylglucosamine-dolichyl-phosphate N-acetylglucosamine phosphotransferase | Initial step in synthesis of dolichol-P-P-oligosacharides | X65603, S41875 |
| O-Glycosylation | O-GlcNAc transferase | | Kreppel et al., 1997, J. Biol. Chem., 272: 9308–9315 |
| Sentrinization | Ubc9 | | Gong et al., 1997, J. Biol. Chem., 272, 28198–28201 |

The several types of post-translational modification presented above will be discussed in some detail below, along with assays to test the enzymes that perform such modifications using natural binding domains and binding partners therefor according to the invention.

ADP-ribosylation

Mono-ADP-ribosylation is a post-translational modification of proteins which is currently thought to play a fundamental role in cellular signalling. A number of mono-ADP-ribosyl-transferases have been identified, including endogenous enzymes from both bacterial and eukaryotic sources and bacterial toxins. A mono-ADP-riboylating enzyme, using as substrates the protein to be modified and nicotinamide adenine dinucleotide ($NAD^+$), is NAD:Arginine ADP ribosyltransferase (Zolkiewska et al., 1992, *Proc. Natl. Acad. Sci, U.S.A.*, 89: 11352–11356). The reactions catalyzed by bacterial toxins such as cholera and pertussis toxin are well understood; the activities of these toxins result in the permanent modification of heterotrimeric G proteins. Endogenous transferases are also thought to modify G proteins and therefore to play a role in signal transduction in the cell (de Murcia et al., 1995, *Trends Cell Biol.*, 78–81). The extent of the effects that ADP-ribosylation can mediate in the cell is illustrated by the example of brefeldin A, a fungal toxin metabolite of palmitic acid. This toxin induces the mono-ADP-ribosylation of BARS-50 (a G protein involved in membrane transport) and glyceraldehyde-3-phosphate dehydrogenase. The cellular effects of brefeldin A include the blocking of constitutive protein secretion and the extensive disruption of the Golgi apparatus. Inhibitors of the brefeldin A mono-ADP-ribosyl-transferase reaction have been shown to antagonise the disassembly of the Golgi apparatus induced by the toxin (Weigert et al., 1997, *J. Biol. Chem.*, 272: 14200–14207). A number of amino acid residues within proteins have been shown to function as ADP-ribose acceptors. Bacterial transferases have been identified which modify arginine, asparagine, cysteine and diphthamide residues in target proteins. Endogenous eukaryotic transferases are known which also modify these amino acids, in addition there is evidence that serine, threonine, tyrosine, hydroxyproline and histidine residues may act as ADP-ribose acceptors but the relevant transferases have not yet been identified (Cervantes-Laurean et al., 1997, *Methods Enzymol.*, 280: 275–287 and references therein).

Poly-ADP-ribosylation is thought to play an important role in events such as DNA repair, replication, recombination and packaging and also in chromosome decondensation. The enzyme responsible for the poly-ADP-ribosylation of proteins involved in these processes is poly (ADP-ribose) polymerase (PARP; for *Drosophila melanogaster* PARP, see Genbank Accession Nos. D13806, D13807 and D13808). The discovery of a leucine zipper in the self-poly(ADP-ribosyl)ation domain of the mammalian PARP (Uchida et al., 1993, *Proc. Natl. Acad. Sci. U.S.A.*, 90: 3481–3485) suggested that this region may be important for the dimerization of PARP and also its interaction with other proteins (Mendoza-Alvarez et al., 1993, *J. Biol. Chem.*, 268: 22575–22580).

Specific examples of ADP ADP-ribosylation sites are those found at $Cys_3$ and $Cys_4$ (underlined) of the B-50 protein (Coggins et al., 1993, *J. Neurochem*, 60: 368–371; Swiss Prot Accession No. P06836):

ML<u>C</u><u>C</u>MRRTKQVEKNDDD          (SEQ ID NO: 16)

and Pγ (the γ subunit of cycylic CMP phophodiesterease; Bondarenko et al., 1997, *J. Biol. Chem.*,

FKQRQTRQFK          (SEQ ID NO: 17)

Two non-limiting examples of assays of enzymatic activity according to the invention which assays are based upon the detection of changes in ADP-ribosylation-dependent protein:protein binding are briefly summarized as follows:

Assay 1

This Assay Employs as Reporter Molecules the Following

Retinal rod cGMP phosphodiesterase γ subunit (Pγ; whole protein, or as little as amino acids 19–87, mutated to remove the phosphorylation site at $Thr_{22}$; Bondarenko, 1997, *J. Biol. Chem.*, 272: 15856–15864; Tsuboi et al., 1994, *J. Biol. Chem.*, 269: 15016–15023; OWL accession no. P04972; Genbank accession no. X04270)

Transducin α subunit (Tα; whole protein, or as little as amino acids 293–314, acetyl-EDAGNYIKVQFLELNMRRDVKE-amide (SEQ ID NO:18); Rarick et al., 1992, *Science*, 256: 1031–1033; OWL accession no. P04695; Genbank no. K03254)

These proteins are components of the vertebrate light-response system, which includes transducin (a heterotrimeric G protein), a cGMP-specific phosphodiesterase (PDE) and rhodopsin. Analogous components can be identified in a number of G protein-coupled signalling systems. Tα-GTP activates its effector, cGMP-PDE, by binding to the inhibitory subunits of that protein and thereby relieving inhibition its enzymatic activity (Stryer, 1986, Ann. Rev. Cell Biol., 2: 391–419). It has been shown that the ADP-ribosylation of Pγ at $Arg_{33}$ or $Arg_{36}$ occurs when Pγ is complexed with Pαβ but not when it is complexed with Tα (Bondarenko et al., 1997, supra). It has been suggested that the sites of ADP-ribosylation are masked in the Pγ-Tα complex. This assay for ADP-ribosylation can be adapted to detect the de-ADP-ribosylation of Pγ. Problems arise because the affinity of Pγ for its alternative partners is affected by other factors including the nucleotide bound to Tα (Tα-GTP has higher affinity for Pγ than does Tα-GDP) and the phosphorylation state of Pγ. This can be overcome by using a Tα peptide to avoid the effects of nucleotide exchange and by using a Pγ peptide lacking the relevant phosphorylation site ($Thr_{22}$; Tsuboi et al., 1994, supra). An α4/β6 loop peptide (amino acids 293–314) has a high affinity for Pγ (Noel et al., 1993, *Nature*, 366: 654–663). The ability of this system to be used as an assay for the ADP-ribosylation reaction depends upon the affinity of the Tα peptide (amino acids 293–314) for Pγ (amino acids 19–87). If binding is too tight, a shorter peptide which has also been reported to stimulate PDE activity (i.e. associate with Pγ; Rarick et. al., 1992, supra) can be used instead.

The design for such an assay is:

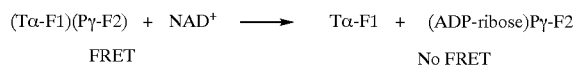

where F1 is the donor fluorophore and F2 is the acceptor.

Placement of Chemical Fluorophores

There are several lysine residues close to the modified arginine residues in the Pγ sequence. Candidates for labelling include $K_{25}$, $K_{41}$, $K_{44}$ and $K_{45}$. The protein has a single C residue, $C_{68}$. Labelling here may simplify the addition of a single fluorophore at a known site.

The Tα peptide has two lysine residues which can be labeled, $K_{300}$ and $K_{313}$. The most appropriate labelling site pairings can be selected based upon such structural information as is available and/or by the empirical testing of labels at various combinations of sites.

Placement of a Fluorescent Protein Label

GFP of another fluorescent protein can be fused to a natural binding domain, sequence or polypeptide and/or its binding partner at either of the C- and N-termini of the two molecules followed by empirical detection of the labeled polypeptides in control protein binding reactions.

Assay 2

The Following Component is Employed in a Homodimerization Assay

Drosophila PARP (whole protein or amino acids 369–994, lacking the zinc finger DNA binding domain; Uchida et al., 1993, *Proc Natl. Acad. Sci. U.S.A.*, 90: 3481–3485; OWL accession no. P35875; Genbank accession nos. D13806, D13807 and D13808).

Drosophila PARP possesses a leucine zipper motif in the self-poly(ADP-ribosyl)ation domain which is also found in the bovine, mouse, chicken and human sequences. Two conserved glutamate residues are predicted to be poly(ADP-ribosylation) auto-modification sites. It has been suggested that poly(ADP-ribosylation) of these sites results in dissociation of the dimer due to the large negative charge of the polymer (Mendoza-Alvarez et al., 1993, supra). A catalytic dimer is required for the reaction to proceed as the auto-modification reaction has been shown to be intermolecular (Mendoza-Alvarez et al., 1993, supra). The leucine zipper domain is predicted to also mediate heterodimerization of PARP; thus, other poly(ADP-ribosylating) binding partners may be useful in this assay of the invention.

Thus the assay would be:

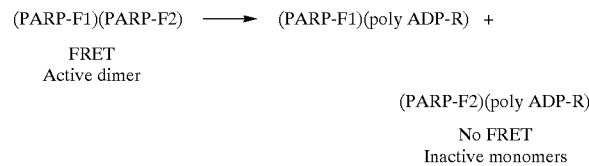

where F1 is the donor fluorophore and F2 is the acceptor.

In reporter molecules of such an assay, chemical fluorophores are located on residue $K_{416}$, just outside the leucine zipper, or on residues in the b, c or f positions of the leucine zipper (e.g. $K_{389}$). If a fluorescent protein (e.g., GFP) is used, it is placed at the N-terminus of the truncated PARP molecule.

Ubiquitination

Ubiquitination of a protein targets the protein for destruction by the proteosome. This process of destruction is very rapid ($t_{1/2}$~60 seconds), and many proteins with rapid turnover kinetics are destroyed via this route. These include cyclins, p53, transcription factors and transcription regulatory factors, among others. Thus, ubiquitination is important in processes such as cell cycle control, cell growth, inflammation, signal transduction; in addition, failure to ubiquitinate proteins in an appropriate manner is implicated in malignant transformation. Ubiquitin is a 76-amino-acid protein which is covalently attached to a target protein by an isopeptide bond, between the ε-amino group of a lysine residue and the C-terminal glycine residue of ubiquitin. Such modification is known as mono-ubiquitination, and this can occur on multiple Lys residues within a target protein. Once attached, the ubiquitin can itself be ubiquitinated, thus forming extended branched chains of polyubiquitin. It is this latter state which signals destruction of the target protein by the proteosome. In the process of destruction, it appears that the polyubiquitinated protein is taken to the proteosome via a molecular chaperone protein, the ubiquitin molecules are removed undamaged (and recycled) and the target is degraded.

Ubiquitination is a complex process, which requires the action of three enzymes: Ubiquitin activating enzyme E1 (for human, Genbank Accession No. X56976), ubiquitin conjugating enzyme E2, also referred to as the ubiquitin carrier protein, (for human 17kDa form, Genbank Accession No. X78140) and Ubiquitin protein ligase E3α (UBR1;

human, Genbank Accession No. AF061556). There are multiple forms of each of these enzymes in the cell, and the above examples are, therefore, non-limiting.

Two examples of ubiquitination sites from natural proteins, IκB (Dai et al., 1998, *J. Biol. Chem.*, 273: 3562–3573; Genbank Accession No. M69043) and β-galactosidase (Johnson et al., 1990, *Nature*, 346: 287–291) are as follows:

IκB NH$_3$-MFQAAERPQEWAMEGPRDGLKKERLLDDRH-COOH (SEQ ID NO:19)

β-galactosidase NH$_3$-HGSGAWLLPVSLVK RKTTLAP-COOH (SEQ ID NO:20)

where the ubiquitinated lysine residue is underlined for each (e.g., Lys$_{15}$ and Lys$_{17}$, for β-acetylglucosamine, Gal=galactose, Xyl=Xylose; Glc=glucose, Man=mannose and Ara=arabinose; Hansen et al., 1995, supra). Intracellular proteins are among the targets for O-glycosylation through the dynamic attachment and removal of O-N-Acetyl-D-glucosamine (O-GlcNAc; reviewed by Hart, 1997, *Ann. Rev. Biochem.*, 66: 315–335). Proteins known to be O-glycosylated include cytoskeletal proteins, transcription factors, the nuclear pore protein complex, and tumor-suppressor proteins (Hart, 1997, supra). Frequently these proteins are also phosphoproteins, and there is a suggestion that O-GlcNAc and phosphorylation of a protein play reciprocal roles. Furthermore, it has been proposed that the glycosylation of an individual protein regulates protein:protein interactions in which it is involved.

According to the invention, a ubiquitination assay measures the addition of ubiquitin to-, rather than the destruction of-, a natural binding domain, sequence or polyeptpide.

Such an assay is summarized briefly below.

The assay components are as follows:

NFκB IκBα and VCP.

NFκB is a transcription factor held in the cytoplasm by the tight association with an inhibitor protein IκBα., or other members of this protein family (Baldwin, 1996, *Ann. Rev. Biochem.*, 14: 648–681). A variety of signals prompt the release of NFκB from IκBα and the subsequent movement of NFκB to the nucleus, where it functions as a transcription factor. IκBα is the first phosphorylated on two residues (Ser$_{32}$ and Ser$_{36}$), which prompts the ubiquitination of IκB on Lys$_{21}$ and other residues; such modification marks IκB for destruction by the proteosome (Dai et al., 1998, *J. Biol. Chem.*, 273: 3562–3573). It has been suggested that following ubiquitination of IκB, a molecular chaperone protein VCP binds to IκB and displaces NFκB (Dai et al., 1998, supra), after which it is surmised that VCP transports IκB to the proteosome for destruction. A fragment of IκB (amino acids 1–242) can participate in the early stages of the above process (i.e., it becomes phosphorylated and ubiquitinated, and binds VCP), but is not then destroyed by proteolysis (Dai, et al., 1998, supra).

An assay for ubiquitination, in this non-limiting example using the natural binding domains found in this pathway, would be:

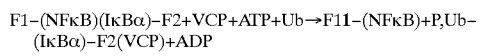
F1–(NFκB)(IκBα)–F2+VCP+ATP+Ub→F11–(NFκB)+P,Ub–(IκBα)–F2(VCP)+ADP

F1 is the donor fluorophore, F2 the acceptor, P is the phosphorylation and Ub is ubiquitin.

If the assay is to be constructed using fragements of the full length proteins, those which comprise natural binding domains (i.e., those which are "binding sequences", as defined above) then the regions of NFκB and IκB of interest are:

For the NFκB p65:p50 Heterodimer p65 (amino acids 12–317) as described as capable of binding IκB (Jaffray et al., 1995, *Mol. Cell. Biol.*, 15: 2166–2172).

p50 (amino acids 39–364; Ghosh et al., 1995, *Nature*, 373: 303–310). This represents the murine sequence (Accession No. M57999, M37732). As an alternative, the human p50 (amino acids 2–366; Muller et al., 1995, *Nature*, 373: 311–317) can be employed.

For IκBα and VCP

IκBα (amino acids 1–305; as deduced from the data of Bell et al., 1996, *Mol. Cell. Biol.*, 16: 6477–6485). The amino acid sequence of IκBαc has been described (Davis et al., 1991, *Science*, 253: 1268–1271). The acidic domain of IκBα, which includes residues 275–300, is required for effective binding to NFκB. VCP, which is an optically inactive part of this assay (i.e. not fluorescently labeled), is used as a whole protein, as functional dissection of VCP has not been described to date.

Placement of Fluorophores (Chemical)

Prior to use in an assay of the invention, a natural binding domain and binding partner used to examine ubiquitination should be labeled at a number of positions and the distance between F1 and F2 optimized empirically. In order to do this, existing residues which can be conjugated with fluorescent dyes may be used. Alternatively, new residues may be introduced by site-directed mutagenesis for the purpose of conjugation with fluorescent dyes; however, such alterations must be made in residues which are not a part of the natural binding domain.

Potential labelling sites on p50 (human sequence) include: K$_{278}$, K$_{275}$, K$_{252}$, K148. These residues appear to be close to the NLS site (Bell et al., 1996, supra), which is believed to form part of the IκBα binding feature, but they are not protected by IκBα binding; thus modification at these positions to accomodate a label should not interfere with binding.

Potential labelling sites on IκBα: Binding sites for NFκB appear to be present within the region of amino acids 200–300 of IκBα (Jaffray et al., 1995, supra). Cys or Lys residues within this region may be used for label attachment, providing they are not within the acidic domain (residues 275–300), which is instrumental in protein:protein binding. Good candidate sites include K$_{242}$, K$_{249}$ and C$_{219}$.

Where to Attach a Fluorescent Protein

For P50 of NFκB (murine amino acids 39–364, human amino acids 2–366 or, alternatively, an intact human or murine protein), the fluorescent protein is fused at the C-terminus of P50. As IκBα binds at the C-terminus of NFκB, the fluroescent protein (e.g., GFP) needs to be in close proximity to the binding site.

For IκBα (full protein or amino acids 1–305) the fluorescent protein is placed at the C-terminus. NFκB binds at the C-terminus of IκBα; therefore, the fluorescent protein should be close to the binding site.

A second assay is configured as follows:

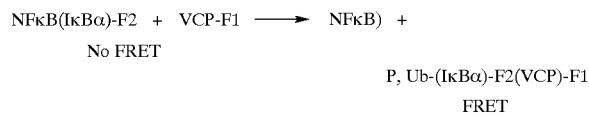
NFκB(IκBα)-F2 + VCP-F1 ⟶ NFκB) +
No FRET
P, Ub-(IκBα)-F2(VCP)-F1
FRET

In this instance, the NFκB is either an intact protein or a partial protein, as described above (see first assay). It is not fluorescently labeled in this assay.

The portion of IκBα of use in the assay is that encompassing amino acids 1–242, as a polypeptide of this sequence can be ubiquitinated, but will not proceed to proteosome destruction (see above; Dai et al., 1998, supra).

The full-length VCP protein is used.

Positioning of the fluorophores (chemical):

IκB is labeled as discussed above in Assay 1.

For VCP, the optimal K or C residues for label attachment must be determined empirically.

Position of a Fluorescent Protein

The C terminus of IκB is fused to the fluorescent protein, as above.

For VCP, the relative suitability of N-terminal and C-terminal attachment of a fluorescent protein (e.g., GFP or a variant thereof) is determined empirically. Alternatively, as structural analysis of VCP is further advanced, the fluorescent protein can be attached to sites outsite of the binding domain.

A third format by which to assay ubiquitination according to the invention involves the binding of (SINA)$_2$ and PHYL to TTK and the subsequent ubiquitination of TTK (and degradation; Li et al., 1997, *Cell*, 90: 469–478). These proteins, which are located in the nucleus, are used whole in assays of the invention.

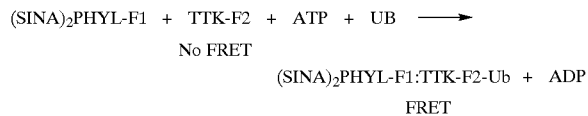

Glycosylatin

N-linked glycosylation is a post-translational modification of proteins which occurs in the endoplasmic reticulum and golgi apparatus and is utilized with some proteins en route for secretion or destined for expression on the cell surface or in another organelle. The carbohydrate moiety is attached to Asn residues in the non-cytoplasmic domains of the target proteins, and the consensus sequence (Shakineshleman, 1996, *Trends Glycosci. Glycotech.*, 8: 115–130) for a glycosylation site is:

NxS/T, where x cannot be proline or aspartic acid. N-linked sugars have a common five-residue core consisting of two GlcNAc residues and three mannose residues due to the biosynthetic pathway. This core is modified by a variety of Golgi enzymes to give three general classes of carbohydrate known as oligomannosyl, hybrid and lactosamine-containing or complex structures (Zubay, 1998, *Biochemist*, Wm. C. Brown Publishers). An enzyme known to mediate N-glycosylation at the initial step of synthesis of dolichyl-P-P-oligosaccharides is UDP-N-Acetylglucosamine-Dolichyl-phosphate-N-acetylsglucosamine phosphotransferase (for mouse, Genbank Accession Nos. X65603 and S41875).

Oxygen-linked glycosylation also occurs in nature with the attachment of various sugar moieties to Ser or Thr residues (Hansen et al., 1995, *Biochem. J.*, 308: 801–813). Complex O-linked glycosylation can be broken into at least six classes—mucin type, ser-α1-GlcNAc; proteoglycan type, ser-Gal-Gal-Xyl core; collagen type hydroxylys-Gal-Glc; clotting factor type, ser-Xyl-Glc or ser-Xyl-Xyl-Glc core; fungal type, ser-Man; plant type, hydroxypro-Ara or ser-Gal (where GlcNAc=N-acetylglucosamine, Gal= galactose, Xyl=Xylose; Glc=glucose, Man=mannose and Ara=arabinose; Hansen et al., 1995, supra). Intracellular proteins are among the targets for O-glycosylation through the dynamic attachment and removal of O-N-Acetyl-D-glucosamine (O-GlcNAc; reviewed by Hart, 1997, *Ann. Rev. Biochem.*, 66: 315–335). Proteins known to be O-glycosylated include cytoskeletal proteins, transcription factors, the nuclear pore protein complex, and tumor-suppressor proteins (Hart, 1997, supra). Frequently these proteins are also phosphoproteins, and there is a suggestion that O-GlcNAc and phosphorylation of a protein play reciprocal roles. Furthermore, it has been proposed that the glycosylation of an individual protein regulates protein:protein interactions in which it is involved.

Specific sites for the addition of O-GlcNAc are found, for example, at Ser$_{277}$, Ser$_{316}$ and Ser$_{383}$ of p67$^{SRF}$ (Reason et. al., 1992, *J. Biol. Chem.*, 267: 16911–16921; Genbank Accession No. J03161). The recognition sequences encompassing these residues are shown below:

| | |
|---|---|
| $^{274}$GTTSTIQTAP | (SEQ ID NO:13) |
| $^{313}$SAVSSADGTVLK | (SEQ ID NO:14) |
| $^{374}$DSSTDLTQTSSSGTVTLP | (SEQ ID NO:15) |

The identity of sites of O-GlcNAc is additionally known for a small number of proteins including c-myc (Thr$_{58}$, also a phosphorylation site; Chou et al., 1995, *J. Biol. Chem.*, 270: 18961–18965), the nucleopore protein p62 (see Reason et al., 1992, supra):

| | |
|---|---|
| MAGGPADTSDPL | (SEQ ID NO:21) | and band 4.1 of the erythrocyte (see Reason et al., 1992, supra):

| | |
|---|---|
| AQTITSETPSSTT | (SEQ ID NO:22) |

The site at which modification occurs is, in each case, underlined. The reaction is mediated by O-GlcNAc transferase (Kreppel et al., 1997, *J. Biol. Chem.*, 272: 9308–9315).

Several non-limiting examples of assay formats useful in the monitoring of glycoslating enzymes according to the invention may be summarized as follows:

Assay 1

The reporter Polypeptides of a First Glycosylation Assay Are

Chicken hepatic lectin (amino acids 49–207, predicted extracellular domain: Burrows et al., 1997, *Biochem. J.*, 324: 673–680; OWL accession no. P02707; Genbank accession no. M63230)

c-Myc (amino acids 1–143, N-terminal transactivation domain; Chou et al., 1995, *J. Biol Chem.*, 270: 18961–18965; OWL accession no. P01107; Genbank accession no. V00568)

Chicken hepatic lectin (CHL) is a type II transmembrane protein which shows almost complete specificity for N-acetylglucosamine, which residue it binds by the C-terminal, extracellular carbohydrate-recognition domain (CRD). The intact receptor probably consists of a trimer of polypeptides stabilized by a coiled-coil structure formed by the transmembrane region and the stalk immediately N-terminal to the (CRD). Molecular modeling suggests, however, that the sugar-binding site is formed by a single polypeptide (Burrows at al., 1997,supra). It is likely that glycosylated c-Myc will bind to the O-GlcNAc at Thr$_{58}$.

c-Myc is a proto-oncogene product playing a role in the control of gene transcription. Mutation or deregulation of the expression of this protein can contribute to malignant transformation of cells. The O-GlcNAcylation of c-Myc at Thr$_{58}$ is thought to be reciprocal to phosphorylation at this site which is also a site of frequent mutation in human lymphomas (Chou et al., 1995, supra).

In addition to its utility in enzymatic assays of the invention, this assay for O-Glc-NAcylation can be adapted to monitor the modification of the large number of cytoplasmic and nuclear proteins thought to undergo O-Glc-NAcylation (Hart, 1997, Ann. Rev. Biochem., 66: 315–35).

Thus, the assay would be:

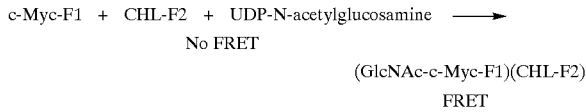

where F1 is the donor fluorophore, and F2 the acceptor fluorophore.

Placement of Chemical Fluorophores

From the molecular model of interaction between CHL and N-acetylglucosamine (based on the MBP-C crystal structure, Burrows et al., 1997, supra; Weis et al., 1992, Nature, 360: 127–134), the binding site is thought to be in the C-terminal region of the domain. Possible labelling sites include $K_{166}$, $E_{,167}$, $E_{202}$ and $K_{207}$.

In the absence of complete structural data for c-Myc, labelling sites must be assayed empirically. $K_{51}$ and $K_{52}$ are close to the glycosylated site, and so labelling at these sites may interfere with the interaction between c-myc and CHL. Other candidate sites include $E_{39}$, $E_{47}$, $R_{66}$, $R_{83}$, $K_{126}$ and $K_{143}$.

Placement of a Fluorescent Protein

In reporter molecules of this glycosylation assay, a fluorescent protein (e.g., Green Fluorescent Protein, GFP) would be placed at the C-terminus of the CHL domain and probably at the N-terminus of the c-Myc transactivation domain. Because in the c-Myc transactivation domain the site of glycosylation is almost equidistant in primary structure from the termini, the most appropriate site would need to be determined empirically in the absence of structural information.

Assay 2

A Second Glycosylation Assay of Use in the Invention Comprises the Following Reporter Molecules Tau (Wang et al., 1996, Nature Medicine, 2: 871–875; OWL accession no. P10636; Genbank accession no. X14474)

Galanthus nivalis agglutinin (Wang et al., 1996, supra; Hester et al., 1995, Nature Structural Biology, 2: 472–479; OWL accession no. P30617; Genbank accession no. M55556)

Tau from the brains of patients with Alzheimer's Disease (AD) has been shown to be glycosylated (determined by lectin binding on Western blots), whereas tau from normal brain tissue shows no sign of such glycosylation. This abnormal post-translational modification has been shown to play a role in the maintenance of the helical twists in the paired helical filament (PHF) structures formed by tau in the AD neuron (Wang et al., 1996, supra); various lectins were used in this study to identify different carbohydrate moieties on the tau protein. Galanthus nivalis agglutinin (GNA) primarily recognizes terminally-linked mannose residues. The use of this protein as an assay for the modification of Tau permits monitoring of the addition of a terminal mannose residue to a carbohydrate chain on this protein. According to certain embodiments of this assay of the invention, the addition of other residues can be monitored by substituting other lectins, with different sugar recognition specificities than that of GNA, for GNA.

The crystal structure of GNA has been determined (Hester at al., 1995, surpa), this indicates that the protein consists of a dimer of dimers with the high affinity mannose binding site formed at the interface between the A and D or, alternatively, B and C subunits. This binding site consists of β-strands donated from the N- and C-terminal regions of one subunit (residues 1–6 and 82–101) and also the C-terminal β-strand from the partner subunit (residues 102–109). It is suggested that the domain structure is indicative of a covalent link between subunits during the evolution of this tetramer (Hester at al., 1995, surpa). The assay can, therefore, be configured using the whole tetrameric assembly with a fluorescent label on only one subunit or potentially as a covalent dimer of subunits, again with one label.

An assay of this type is diagrammed as follows:

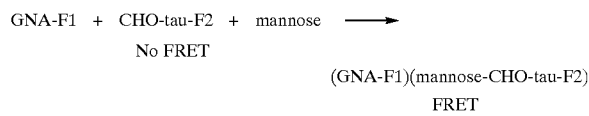

where F1 is the donor fluorophore and F2 is the acceptor. CHO represents the glycosylation of tau prior to addition of the terminal mannose.

Tau protein contains a number of residues which can be labeled, of which the most favorable must be determined empirically.

A number of potential labelling sites exist within the GNA subdomain which participates in high-affinity mannose binding. These include $D_1$, $K_{90}$ (which residue is very close to the site of interaction with the mannose residue), $D_{100}$ and $R_{101}$. Alternatively, a short C-terminal extension can bear a labelling site.

As above, the site for fusion of GFP to tau is to be determined empirically. Labelling of the GNA subdomain on either the C- or N-terminus is equally effective.

Prenylation (Fatty Acylation)

The post-translational modification of proteins with fatty acids includes the attachment of myristic acid to the primary amino group of an N-terminal glycine residue (Johnson et al., 1994, Ann. Rev. Biochem., 63: 869–914) and the attachment of palmitic acid to cysteine residues (Milligan et al., 1995, Trends Biochem. Sci., 20: 181–186).

Fatty acylation of proteins is a dynamic post-translational modification which is critical for the biological activity of many proteins, as well as their interactions with other proteins and with membranes. Thus, for a large number of proteins, the location of the protein within a cell can be controlled by its state of prenylation (fatty acid modification) as can its ability to interact with effector enzymes (ras and MAP kinase, Itoh et al., 1993, J. Biol. Chem., 268: 3025-; ras and adenylate cyclase (in yeast; Horiuchi et al., 1992, Mol. Cell. Biol., 12: 4515-) or with regulatory proteins (Shirataki et al., 1991, J. Biol, Chem., 266: 20672–20677). The prenylation status of ras is important for its oncogenic properties (Cox, 1995, Methods Enzymol., 250: 105–121) thus interference with the prenylation status of ras is considered a valuable anti-cancer strategy (Hancock, 1993, Curr. Biol., 3: 770).

Sentrinization

Sentrin is a novel 101-amino acid protein which has 18% identity and 48% similarity with human ubiquitin (Okura et al., 1996, J.Immunol, 157: 4277–4281). This protein is known by a number of other names including SUMO-1, UBL1, PIC1, GMP1 and SMT3C and is one of a number of ubiquitin-like proteins that have recently been identified. Sentrin is expressed in all tissues (as shown by Northern blot analysis), but mRNA levels are higher in the heart, skeletal muscle, testis, ovary and thymus.

The sentrinization of proteins is thought to involve the Ubiquitin-conjugating enzyme Ubc9 (Gong et al., 1997, *J. Biol. Chem.*, 272: 28198–28201). The interaction between these two proteins in the yeast two-hybrid screen is very specific, suggesting that this is a biologically relevant phenomenon. The interaction is dependent upon the presence of the conserved C-terminal Gly-Gly residues present in sentrin (Gong et al., 1997, supra). The conjugation of sentrin to other proteins via $Gly_{97}$ requires the cleavage of the C-terminal four amino acids of the protein, His-Ser-Thr-Val.

One important protein shown to be modified by the addition of sentrin is the Ran-specific GTPase-activating protein, RanGAP1, which is involved in nuclear import of proteins bearing nuclear-localization signals (Johnson and Hochstrasser, 1997, *Trends Cell Biol.*, 7: 408–413). Conjugation of RanGAP1 and sentrin is essential both for the targeting of RanGAP1 to its binding partner on the nuclear pore complex (NPC) and for the nuclear import of proteins. Sentrin itself does not bind with high affinity to the NPC and it is, therefore, likely that it either provokes a conformational change in RanGAP1 that exposes a binding site or, alternatively, that the binding site is formed using both sentrin and RanGAP1 sequences. There is evidence to suggest that the conjugation of sentrin to RanGAP1 is necessary for the formation of other sentrinized proteins (Kamitani et al., 1997, *J. Biol. Chem.*, 272: 14001–14004) and that the majority of these sentrinized proteins are found in the nucleus.

Sentrin has been shown in yeast two-hybrid screens to interact with a number of other proteins, including the death domains of Fas/APO1 and the TNF receptors, PML, RAD51 and RAD52 (Johnson and Hochstrasser, 1997, supra). These interactions implicate sentrin in a number of important processes. Fas/APO1 and TNF receptors are involved in transducing the apoptosis signal via their death domains. Ligation of Fas on the cell surface results in the formation of a complex via death domains and death-effector domains, triggering the induction of apoptosis. The overexpression of sentrin protects cells from both anti-Fas/APO and TNF-induced cell death (Okura et al., 1996, supra). It is not clear whether this protection is achieved simply by preventing the binding of other proteins to these death domains or whether a more complex process is involved, possibly one involving the ubiquitin pathway.

The interaction of sentrin with PML (a RING finger protein) is important, as it points to a disease state in which this protein may play a role. In normal myeloid cells, PML is found in a nuclear multiprotein complex known as a nuclear body. These nuclear bodies are disrupted in acute promyelocytic leukaemia, where a chromosomal translocation generates a fusion between regions of the retinoic acid receptor α and PML. This disruption can be reversed by treatment with retinoic acid. It has been shown that PML is covalently modified at multiple sites by members of the sentrin family of proteins (but not by ubiquitin or NEDD8). Two forms of the abberent fusion protein have been identified, neither of which is modified by sentrin. It is, therefore, thought that differential sentrinization of the normal and abberant forms of PML may be important in the processes underlying acute promyelocytic leukaemia and may help in the understanding of the biological role of the PML protein (Kamitani et al., 1998, *J. Biol. Chem.*, 273: 3117–3120).

D. Methods for Detection of Protein Modification in Real Time i. In vitro Protein Modification and Detection Thereof Modifying Enzymes The invention requires the presence of a modifying enzyme which catalyzes either the addition or removal of a modifying group. A range of modifying enzymes are available commercially (e.g. from Sigma, St. Louis, Mo.; Promega, Madison, Wis.; Boehringer Mannheim Biochemicals, Indianapolis, Ind.; New England Biolabs, Beverly, Mass.; and others). Alternatively, such enzymes may be prepared in the laboratory by methods well known in the art.

General methods of preparing pure and partially-purified recombinant proteins, as well as crude cellular extracts comprising such proteins, are well known in the art. Molecular methods useful in the production of recombinant proteins, whether such proteins are the enzymes to be assayed according to the invention or the labeled reporter polypeptides comprising a coiled-coil of the invention, are well known in the art (for methods of cloning, expression of cloned genes and protein purification, see Sambrook et al., 1989, *Molecular Cloning, A Laboratory Manual.*, 2nd Edition, Cold Spring Harbor Laboratory Press, Cold Spring Harbor, N.Y.; Ausubel et al., *Current Protocols in Molecular Biology*, copyright 1987–1994, Current Protocols, copyright 1994–1998, John Wiley & Sons, Inc.).

According to the invention, assays of the activity of protein-modifying enzymes may be performed using crude cellular extracts, whether to test the activity of a recombinant protein or one which is found in nature, such as in a biological sample obtained from a test cell line or animal or from a clinical patient. In the former case, use of a crude cell extract enables rapid screening of many samples, which potentially finds special application in high-throughput screening methods, e.g. of candidate modulators of protein-modifying enzyme activity. In the latter case, use of a crude extract with the labeled reporter polypeptide comprising a natural binding domain and, for at least one member of a pair of binding partners, a natural site for post-translational protein modification of the invention facilitates easy and rapid assessment of the activity of an enzyme of interest in a diagnostic procedure, e.g., one which is directed at determining whether a protein-modifying enzyme is active at an a physiologically-appropriate level, or in a procedure designed to assess the efficacy of a therapy aimed at modulating the activity of a particular enzyme.

Production of Polypeptides of Use in the Invention

A polypeptide consisting of—or comprising a natural binding domain or a binding partner therefor may be synthesized by Fmoc or Tboc chemistry according to methods known in the art (e.g., see Atherton et al., 1981, *J. Chem. Soc. Perkin I*, 1981(2): 538–546; Merrifield, 1963, *J. Am. Chem. Soc.*, 85: 2149–2154, respectively). Following deprotection and cleavage from the resin, peptides are desalted by gel filtration chromatography and analyzed by mass spectroscopy, HPLC, Edman degradation and/or other methods as are known in the art for protein sequencing using standard methodologies.

Alternatively, nucleic acid sequences encoding such peptides may be expressed either in cells or in an in vitro transcription/translation system (see below) and, as with enzymes to be assayed according to the invention, the proteins purified by methods well known in the art.

Labelling a Natural Binding Domain and/or a Binding Partner Therefor with a Detectable Label A natural binding domain or binding partner therefor may be labeled with thiol reactive derivatives of fluorescein and tetramethylrhodamine (isothiocyanate or iodoacetamide derivatives, Molecular Probes, Eugene, Oreg., USA) using procedures described by Hermanson G. T., 1995, *Bioconjugate Techniques*, Academic Press, London. Alternatively, primary-amine-directed conjugation reactions can be used to label lysine sidechains or the free peptide N-terminus (Hermason, 1995, supra).

Purification of Fluorescent Peptides

Fluorescent peptides are separated from unreacted fluorophores by gel filtration chromatography or reverse phase HPLC.

Fluorescence Measurements of Protein Modification in vitro in Real Time

Donor and acceptor fluorophore-labeled natural binding domains and the corresponding binding partners for any such natural molecules (molar equivalents of fluorophore-labeled polypeptide or molar excess of acceptor-labeled polypeptide) are first mixed (if the two are present on separate polypeptides). Samples are analyzed in a fluorimeter using excitation wavelengths relevant to the donor fluorescent label and emission wavelengths relevant to both the donor and acceptor labels. A ratio of emission from the acceptor over that from the donor following excitation at a single wavelength is used to determine the efficiency of fluorescence energy transfer between fluorophores, and hence their spatial proximity. Typically, measurements are performed at 0–37° C. as a function of time following the addition of the modifying enzyme (and, optionally, a modulator or candidate modulator of function for that enzyme, as described below) to the system in 50 mM histidine pH 7.0, 120 mM KCl, 5 mM $MgSO_4$, 5 mM NaF, 0.05 mM EGTA and 0.2 mM ATP. The assay may be performed at a higher temperature if that temperature is compatible with the enzyme(s) under study.

Alternative Cell-free Assay System of the Invention

A cell-free assay system must permit binding of a natural binding domain to its binding partner to occur in a modification-dependent manner. As indicated herein, such a system may comprise a low-ionic-strength buffer (e.g., physiological salt, such as simple saline or phosphate- and/or Tris-buffered saline or other as described above), a cell culture medium, of which many are known in the art, or a whole or fractionated cell lysate. The components of an assay of post-translational modification of a polypeptide molecule according to the invention may be added into a buffer, medium or lysate or may have been expressed in cells from which a lysate is derived. Alternatively, a cell-free transcription- and/or translation system may be used to deliver one or more of these components to the assay system. Nucleic acids of use in cell-free expression systems according to the invention are as described for in vivo assays, below.

An assay of the invention may be peformed in a standard in vitro transcription/translation system under conditions which permit expression of a recombinant or other gene. The TNT® T7 Quick Coupled Transcription/Translation System (Cat. # L1170; Promega) contains all reagents necessary for in vitro transcription/translation except the DNA of interest and the detection label; as discussed below, a natural binding domain and/or its binding partner may be encoded by expression constructs in which their coding sequences are fused in-frame to those encoding fluorescent proteins. The TNT® Coupled Reticulocyte Lysate Systems (comprising a rabbit reticulocyte lysate) include: TNT® T3 Coupled Reticulocyte Lysate System (Cat. # L4950; Promega); TNT® T7 Coupled Reticulocyte Lysate System (Cat. # L4610; Promega); TNT® SP6 Coupled Reticulocyte Lysate System (Cat. # L4600; Promega); TNT® T7/SP6 Coupled Reticulocyte Lysate System (Cat. # L5020; Promega); TNT® T7/T3 Coupled Reticulocyte Lysate System (Cat. # L5010; Promega).

An assay involving a cell lysate or a whole cell (see below) may be performed in a cell lysate or whole cell preferably eukaryotic in nature (such as yeast, fungi, insect, e.g., Drosophila), mouse, or human). An assay in which a cell lysate is used is performed in a standard in vitro system under conditions which permit gene expression. A rabbit reticulocyte lysate alone is also available from Promega, either nuclease-treated (Cat. # L4960) or untreated (Cat. # L4151).

Candidate Modulators of Protein-modifying Enzymes to be Screened According to the Invention Whether in vitro or in an in vivo system (see below), the invention encompasses methods by which to screen compositions which may enhance, inhibit or not affect (e.g., in a cross-screening procedure in which the goal is to determine whether an agent intended for one purpose additionally affects general cellular functions, of which protein modification is an example) the activity of a protein-modifying enzyme.

Candidate modulator compounds from large libraries of synthetic or natural compounds can be screened. Numerous means are currently used for random and directed synthesis of saccharide, peptide, and nucleic acid based compounds. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are available and can be prepared. Alternatively, libraries of natural compounds in the form of bacterial, fungal, plant and animal extracts are available from e.g., Pan Laboratories (Bothell, Wash.) or MycoSearch (NC), or are readily produceable by methods well known in the art. Additionally, natural and synthetically produced libraries and compounds are readily modified through conventional chemical, physical, and biochemical means.

Useful compounds may be found within numerous chemical classes, though typically they are organic compounds, including small organic compounds. Small organic compounds have a molecular weight of more than 50 yet less than about 2,500 daltons, preferably less than about 750, more preferably less than about 350 daltons. Exemplary classes include heterocycles, peptides, saccharides, steroids, and the like. The compounds may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxylic terminus, e.g. for the amino group, acylation or alkylation, and for the carboxyl group, esterification or amidification, or the like.

Candidate modulators which may be screened according to the methods of the invention include receptors, enzymes, ligands, regulatory factors, and structural proteins. Candidate modulators also include nuclear proteins, cytoplasmic proteins, mitochondrial proteins, secreted proteins, plasmalemma-associated proteins, serum proteins, viral antigens, bacterial antigens, protozoal antigens and parasitic antigens. Candidate modulators additionally comprise proteins, lipoproteins, glycoproteins, phosphoproteins and nucleic acids (e.g., RNAs such as ribozymes or antisense nucleic acids). Proteins or polypeptides which can be screened using the methods of the present invention include hormones, growth factors, neurotransmitters, enzymes, clotting factors, apolipoproteins, receptors, drugs, oncogenes, tumor antigens, tumor suppressors, structural proteins, viral antigens, parasitic antigens, bacterial antigens and antibodies (see below).

Candidate modulators which may be screened according to the invention also include substances for which a test cell or organism might be deficient or that might be clinically effective in higher-than-normal concentration as well as those that are designed to eliminate the translation of unwanted proteins. Nucleic acids of use according to the invention not only may encode the candidate modulators described above, but may eliminate or encode products which eliminate deleterious proteins. Such nucleic acid sequences are antisense RNA and ribozymes, as well as DNA expression constructs that encode them. Note that antisense RNA molecules, ribozymes or genes encoding them may be administered to a test cell or organism by a method of nucleic acid delivery that is known in the art, as described below. Inactivating nucleic acid sequences may encode a ribozyme or antisense RNA specific for the a target mRNA. Ribozymes of the hammerhead class are the smallest known, and lend themselves both to in vitro production and delivery to cells (summarized by Sullivan, 1994, *J. Invest. Dermatol.*, 103: 85S–98S; Usman et al., 1996, *Curr. Opin. Struct. Biol.*, 6: 527–533).

As stated above, antibodies are of use in the invention as modulators (specifically, as inhibitors) of protein-modifying enzymes. Methods for the preparation of antibodies are well known in the art, and are briefly summarized as follows:

Either recombinant proteins or those derived from natural sources can be used to generate antibodies using standard techniques, well known to those in the field. For example, the proteins are administered to challenge a mammal such as a monkey, goat, rabbit or mouse. The resulting antibodies can be collected as polyclonal sera, or antibody-producing cells from the challenged animal can be immortalized (e.g. by fusion with an immortalizing fusion partner) to produce monoclonal antibodies.

1. Polyclonal Antibodies.

The antigen protein may be conjugated to a conventional carrier in order to increases its immunogenicity, and an antiserum to the peptide-carrier conjugate is raised. Coupling of a peptide to a carrier protein and immunizations may be performed as described (Dymecki et al., 1992, *J. Biol. Chem.*, 267: 4815–4823). The serum is titered against protein antigen by ELISA (below) or alternatively by dot or spot blotting (Boersma and Van Leeuwen, 1994, *J. Neurosci. Methods*, 51: 317). At the same time, the antiserum may be used in tissue sections prepared as described below. The serum is shown to react strongly with the appropriate peptides by ELISA, for example, following the procedures of Green et al., 1982, *Cell*, 28: 477–487.

2. Monoclonal Antibodies.

Techniques for preparing monoclonal antibodies are well known, and monoclonal antibodies may be prepared using a candidate antigen whose level is to be measured or which is to be either inactivated or affinity-purified, preferably bound to a carrier, as described by Arnheiter et al., *Nature*, 294, 278–280 (1981).

Monoclonal antibodies are typically obtained from hybridoma tissue cultures or from ascites fluid obtained from animals into which the hybridoma tissue is introduced. Nevertheless, monoclonal antibodies may be described as being "raised to" or "induced by" a protein.

Monoclonal antibody-producing hybridomas (or polyclonal sera) can be screened for antibody binding to the target protein. By antibody, we include constructions using the binding (variable) region of such an antibody, and other antibody modifications. Thus, an antibody useful in the invention may comprise a whole antibody, an antibody fragment, a polyfunctional antibody aggregate, or in general a substance comprising one or more specific binding sites from an antibody. The antibody fragment may be a fragment such as an Fv, Fab or F(ab')$_2$ fragment or a derivative thereof, such as a single chain Fv fragment. The antibody or antibody fragment may be non-recombinant, recombinant or humanized. The antibody may be of an immunoglobulin isotype, e.g., IgG, IgM, and so forth. In addition, an aggregate, polymer, derivative and conjugate of an immunoglobulin or a fragment thereof can be used where appropriate.

Determnination of Activity of Candidate Modulator of a Protein-modifying Enzyme

A candidate modulator of the activity of a protein-modifying enzyme may be assayed according to the invention as described herein, is determined to be effective if its use results in a difference of about 10% or greater relative to controls in which it is not present (see below) in FRET or other signal emanating from a detectable label of use in the invention resulting from the association of a natural binding domain with its binding partner in the presence of a protein-modifying enzyme.

The level of activity of a candidate modulator may be quantified using any acceptable limits, for example, via the following formula:

$$\text{Percent Modulation} = \frac{(\text{Index}_{Control} - \text{Index}_{Sample})}{(\text{Index}_{Control})} \times 100$$

where Index$_{Control}$ is the quantitative result (e.g., amount of—or rate of change in fluorescence at a given frequency, rate of molecular rotation, FRET, rate of change in FRET or other index of modification, including, but not limited to, enzyme inhibition or activation) obtained in assays that lack the candidate modulator (in other words, untreated controls), and Index$_{Sample}$ represents the result of the same measurement in assays containing the candidate modulator. As described herein, control measurements are made with a differentially-labeled natural binding domain and its corresponding partner only and with these molecules plus a protein-modifying enzyme which recognizes a natural site for post-translational protein modification present on the natural binding domain and, optionally, on the binding partner.

Such a calculation is used in either in vitro or in vivo assays performed according to the invention.

ii. In vivo Assays of Enzymatic Activity According to the Invention

Reporter Group Protein Modification in Living Cells

Differentially-labeled natural binding domains and binding partners of the invention are delivered (e.g., by microinjection) to cells, such as smooth muscle cells (DDT1) or ventricular cardiac myocytes as previously described (Riabowol et al., 1988, *Cold Spring Harbor Symposia on Quantitative Biology*, 53: 85–90). The ratio of emission from the labeled molecule(s) is measured as described above via a photomultiplier tube focused on a single cell. As described elsewhere herein, an ADP ribosylating enzyme may be stimulated with cholera toxin (G-protein recognition feature) or with brefeldin A.

Heterologous Expression of Peptides

Natural binding domains and/or binding partners therefor can be chemically synthesized, as described above, or may be produced from the heterologous expression of DNA sequences which encode them. Expression can be in procaryotic or eukaryotic cells using a variety of plasmid vectors capable of instructing heterologous expression. Purification of these products is achieved by destruction of the cells (e.g. French Press) and chromatographic purification of the products. This latter procedure can be simplified by the inclusion of an affinity purification tag at one extreme of the peptide, separated from the peptide by a protease cleavage site if necessary.

The Use of Cells or Whole Organisms in Assays of the Invention

When performed using cells, the assays of the invention are broadly applicable to a host cell susceptible to transfection or transformation including, but not limited to, bacteria (both gram-positive and gram-negative), cultured- or explanted plant (including, but not limited to, tobacco, arabidopsis, carnation, rice and lentil cells or protoplasts), insect (e.g., cultured Drosophila or moth cell lines) or vertebrate cells (e.g., mammalian cells) and yeast.

Organisms are currently being developed for the expression of agents including DNA, RNA, proteins, non-proteinaceous compounds, and viruses. Such vector microorganisms include bacteria such as Clostridium (Parker et al., 1947, *Proc. Soc. Exp. Biol. Med.,* 66: 461–465; Fox et al., 1996, *Gene Therapy,* 3: 173–178; Minton et al., 1995, *FEMS Microbiol. Rev.,* 17: 357–364), Salmonella (Pawelek et al., 1997, *Cancer Res.,* 57: 4537–4544; Saltzman et al., 1996, *Cancer Biother. Radiopharm.,* 11: 145–153; Carrier et al., 1992, *J. Immunol.,* 148: 1176–1181; Su et al., 1992, *Microbiol, Pathol.,* 13: 465–476; Chabalgoity et al., 1996, *Infect. Immunol.,* 65: 2402–2412), Listeria (Schafer et al., 1992, *J. Immunol.,* 149: 53–59; Pan et al., 1995, *Nature Med.,* 1: 471–477) and Shigella (Sizemore et al., 1995, *Science,* 270: 299–302), as well as yeast, mycobacteria, slime molds (members of the taxa Dictyosteliida—such as of the genera Polysphondylium and Dictystelium, e.g. *Dictyostelium discoideum*—and Myxomycetes—e.g. of the genera Physarum and Didymium) and members of the Domain Arachaea (including, but not limited to, archaebacteria), which have begun to be used in recombinant nucleic acid work, members of the phylum Protista, or other cell of the algae, fungi, or any cell of the animal or plant kingdoms.

Plant cells useful in expressing polypeptides of use in assays of the invention include, but are not limited to, tobacco (*Nicotiana plumbaginifolia* and *Nicotiana tabacum*), arabidopsis (*Arabidopsis thaliana*), Aspergillus niger, Brassica napus, Brassica nigra, Datura innoxia, Vicia narbonensis, Vicia faba, pea (*Pisum sativum*), cauliflower, carnation and lentil (*Lens culinaris*). Either whole plants, cells or protoplasts may be transfected with a nucleic acid of choice. Methods for plant cell transfection or stable transformation include inoculation with *Agrobacterium tumefaciens* cells carrying the construct of interest (see, among others, Turpen et al., 1993, *J. Virol. Methods,* 42: 227–239), administration of liposome-associated nucleic acid molecules (Maccarrone et al., 1992, *Biochem. Biophys. Res. Commun.,* 186: 1417–1422) and microparticle injection (Johnston and Tang, 1993, *Genet. Eng.* (N.Y.), 15: 225–236), among other methods. A generally useful plant transcriptional control element is the cauliflower mosaic virus (CaMV) 35S promoter (see, for example, Saalbach et al., 1994, *Mol. Gen. Genet.,* 242: 226–236). Non-limiting examples of nucleic acid vectors useful in plants include pGSGLUC1 (Saalbach et al., 1994, supra), pGA492 (Perez et al., 1989, *Plant Mol. Biol.,* 13: 365–373), pOCA18 (Olszewski et al., 1988, *Nucleic Acids Res.,* 16: 10765–10782), the Ti plasmid (Roussell et al., 1988, *Mol. Gen. Genet.,* 211: 202–209) and pKR612B1 (Balazs et al., 1985, *Gene,* 40: 343–348).

Mammalian cells are of use in the invention. Such cells include, but are not limited to, neuronal cells (those of both primary explants and of established cell culture lines) cells of the immune system (such as T-cells, B-cells and macrophages), fibroblasts, hematopoietic cells and dendritic cells. Using established technologies, stem cells (e.g. hematopoietic stem cells) may be used for gene transfer after enrichment procedures. Alternatively, unseparated hematopoietic cells and stem cell populations may be made susceptible to DNA uptake. Transfection of hematopoietic stem cells is described in Mannion-Henderson et al., 1995, *Exp. Hematol,* 23: 1628; Schiffmann et al., 1995, *Blood,* 86: 1218; Williams, 1990, *Bone Marrow Transplant,* 5: 141; Boggs, 1990, *Int. J. Cell Cloning,* 8: 80; Martensson et al., 1987, *Eur. J. Immunol.,* 17: 1499; Okabe et al., 1992, *Eur. J. Immunol.,* 22: 37–43; and Banerji et al., 1983, *Cell,* 33: 729. Such methods may advantageously be used according to the present invention.

Nucleic Acid Vectors for the Expression of Assay Components of the Invention in Cells or Multicellular Organisms A nucleic acid of use according to the methods of the invention may be either double- or single stranded and either naked or associated with protein, carbohydrate, proteoglycan and/or lipid or other molecules. Such vectors may contain modified and/or unmodified nucleotides or ribonucleotides. In the event that the gene to be transfected may be without its native transcriptional regulatory sequences, the vector must provide such sequences to the gene, so that it can be expressed once inside the target cell. Such sequences may direct transcription in a tissue-specific manner, thereby limiting expression of the gene to its target cell population, even if it is taken up by other surrounding cells. Alternatively, such sequences may be general regulators of transcription, such as those that regulate housekeeping genes, which will allow for expression of the transfected gene in more than one cell type; this assumes that the majority of vector molecules will associate preferentially with the cells of the tissue into which they were injected, and that leakage of the vector into other cell types will not be significantly deleterious to the recipient mammal. It is also possible to design a vector that will express the gene of choice in the target cells at a specific time, by using an inducible promoter, which will not direct transcription unless a specific stimulus, such as heat shock, is applied.

A gene encoding a component of the assay system of the invention or a candidate modulator of protein-modifying enzyme activity may be transfected into a cell or organism using a viral or non-viral DNA or RNA vector, where non-viral vectors include, but are not limited to, plasmids, linear nucleic acid molecules, artificial chromomosomes and episomal vectors. Expression of heterologous genes in mammals has been observed after injection of plasmid DNA into muscle (Wolff J. A. et al., 1990, *Science,* 247: 1465–1468; Carson D. A. et al., U.S. Pat. No. 5,580,859), thyroid (Sykes et al., 1994, *Human Gene Ther.,* 5: 837–844), melanoma (Vile et al., 1993, *Cancer Res.,* 53: 962–967), skin (Hengge et al., 1995, *Nature Genet.,* 10: 161–166), liver (Hickman et al., 1994, *Human Gene Therapy,* 5: 1477–1483) and after exposure of airway epithelium (Meyer et al., 1995, *Gene Therapy,* 2: 450–460).

In addition to vectors of the broad classes described above and the natural binding domain- or binding partner/fluorescent protein fusion gene expression constructs described above, microbial plasmids, such as those of bacteria and yeast, are of use in the invention.

Bacterial Plasmids

Of the frequently used origins of replication, pBR322 is useful according to the invention, and pUC is preferred. Although not preferred, other plasmids which are useful according to the invention are those which require the presence of plasmid encoded proteins for replication, for example, those comprising pT181, FII, and FI origins of replication.

Examples of origins of replication which are useful in assays of the invention in E. coli and S. typhimurium include but are not limited to, pHETK (Garapin et al., 1981, Proc. Natl. Acad. Sci. U.S.A., 78: 815–819), p279 (Talmadge et al., 1980, Proc. Natl. Acad. Sci. U.S.A., 77: 3369–3373), p5-3 and p21A-2 (both from Pawalek et al., 1997, Cancer Res., 57: 4537–4544), pMB1 (Bolivar et al., 1977, Gene, 2: 95–113), ColE1 (Kahn et al., 1979, Methods Enzymol., 68: 268–280), p15A (Chang et al., 1978, J. Bacteriol., 134: 1141–1156); pSC101 (Stoker et al., 1982, Gene, 18: 335–341); R6K (Kahn et al., 1979, supra); R1 (temperature dependent origin of replication, Uhlin et al., 1983, Gene, 22: 255–265); lambda dv (Jackson et al., 1972, Proc. Nat. Aca. Sci. U.S.A., 69: 2904–2909); pYA (Nakayama et al., 1988, infra). An example of an origin of replication that is useful in Staphylococcus is pT181 (Scott, 1984, Microbial Reviews 48: 1–23). Of the above-described origins of replication, pMB1, p15A and ColE1 are preferred because these origins do not require plasmid-encoded proteins for replication.

Yeast Plasmids

Three systems are used for recombinant plasmid expression and replication in yeasts:

1. Integrating. An example of such a plasmid is YIp, which is maintained at one copy per haploid genome, and is inherited in Mendelian fashion. Such a plasmid, containing a gene of interest, a bacterial origin of replication and a selectable gene (typically an antibiotic-resistance marker), is produced in bacteria. The purified vector is linearized within the selectable gene and used to transform competent yeast cells. Regardless of the type of plasmid used, yeast cells are typically transformed by chemical methods (e.g. as described by Rose et al., 1990, Methods in Yeast Genetics, Cold Spring Harbor Laboratory Press, Cold Spring Harbor, N.Y.). The cells are treated with lithium acetate to achieve transformation efficiencies of approximately $10^4$ colony-forming units (transformed cells)/μg of DNA. Yeast perform homologous recombination such that the cut, selectable marker recombines with the mutated (usually a point mutation or a small deletion) host gene to restore function. Transformed cells are then isolated on selective media.

2. Low copy-number ARS-CEN, of which YCp is an example. Such a plasmid contains the autonomous replicating sequence (ARS1), a sequence of approximately 700 bp which, when carried on a plasmid, permits its replication in yeast, and a centromeric sequence (CEN4), the latter of which allows mitotic stability. These are usually present in 1–2 copies per cell. Removal of the CEN sequence yields a YRp plasmid, which is typically present in 100–200 copes per cell; however, this plasmid is both mitotically and meiotically unstable.

3. High-copy-number 2μ circles. These plasmids contain a sequence approximately 1 kb in length, the 2μ sequence, which acts as a yeast replicon giving rise to higher plasmid copy number; however, these plasmids are unstable and require selection for maintenance. Copy number is increased by having on the plasmid a selection gene operatively linked to a crippled promoter. This is usually the LEU2 gene with a truncated promoter (LEU2-d), such that low levels of the Leu2p protein are produced; therefore, selection on a leucine-depleted medium forces an increase in copy number in order to make an amount of Leu2p sufficient for cell growth.

As suggested above, examples of yeast plasmids useful in the invention include the YRp plasmids (based on autonomously-replicating sequences, or ARS) and the YEp plasmids (based on the 2μ circle), of which examples are YEp24 and the YEplac series of plasmids (Gietz and Sugino, 1988, Gene, 74: 527–534). (See Sikorski, "Extrachromsomoal cloning vectors of Saccharomyces cerevisiae", in Plasmids, A Practical Approach, Ed. K. G. Hardy, IRL Press, 1993; and Yeast Cloning Vectors and Genes, Current Protocols in Molecular Biology, Section II, Unit 13.4, Eds., Ausubel et al., 1994).

In addition to a yeast origin of replication, yeast plasmid sequences typically comprise an antibiotic resistance gene, a bacterial origin of replication (for propagation in bacterial cells) and a yeast nutritional gene for maintenance in yeast cells. The nutritional gene (or "auxotrophic marker") is most often one of the following (with the gene product listed in parentheses and the sizes quoted encompassing the coding sequence, together with the promoter and terminator elements required for correct expression):

TRP1 (PhosphoADP-ribosylanthranilate isomerase, which is a component of the tryptophan biosynthetic pathway).

URA3 (Orotidine-5'-phosphate decarboxylase, which takes part in the uracil biosynthetic pathway).

LEU2 (3-Isopropylmalate dehydrogenase, which is involved with the leucine biosynthetic pathway).

HIS3 (Imidazoleglycerolphosphate dehydratase, or IGP dehydratase).

LYS2 (α-aminoadipate-semialdehyde dehydrogenase, part of the lysine biosynthetic pathway).

Alternatively, the screening system may operate in an intact, living multicellular organism, such as an insect or a mammal. Methods of generating transgenic Drosophila, mice and other organisms, both transiently and stably, are well known in the art; detection of fluorescence resulting from the expression of Green Fluorescent Protein in live Drosophila is well known in the art. One or more gene expression constructs encoding one or more of a labeled natural binding domain, a binding partner, a protein-modifying enzyme and, optionally, a candidate modulator thereof are introduced into the test organism by methods well known in the art (see also below). Sufficient time is allowed to pass after administration of the nucleic acid molecule to allow for gene expression, for binding of a natural binding domain to its binding partner and for chromophore maturation, if necessary (e.g., Green Fluorescent Protein matures over a period of approximately 2 hours prior to fluorescence) before fluorescence or other emission from a detectable label is measured. A reaction component (particularly a candidate modulator of enzyme function) which is not administered as a nucleic acid molecule may be delivered by a method selected from those described below.

Dosage and Administration of a Labeled natural Binding Domain, Binding Partner Therefor, Protein-modifying Enzyme or Candidate Modulator Thereof for Use in an in vivo Assay of the Invention Dosage For example, the amount of each labeled natural binding domain or binding partner therefor must fall within the detection limits of the fluorescence-measuring device employed. The amount of an enzyme or candidate modulator thereof will typically be in the range of about 1 µg–100 mg/kg body weight. Where the candidate modulator is a peptide or polypeptide, it is typically administered in the range of about 100–500 µg/ml per dose. A single dose of a candidate modulator, or multiple doses of such a substance, daily, weekly, or intermittently, is contemplated according to the invention.

A candidate modulator is tested in a concentration range that depends upon the molecular weight of the molecule and the type of assay. For example, for inhibition of protein/protein or protein/DNA complex formation or transcription initiation (depending upon the level at which the candidate modulator is thought or intended to modulate the activity of a protein modifying enzyme according to the invention), small molecules (as defined above) may be tested in a concentration range of 1 pg–100 µg/ml, preferably at about 100 pg–10 ng/ml; large molecules, e.g., peptides, may be tested in the range of 10 ng–100 µg/ml, preferably 100 ng–10 µg/ml.

Administration

Generally, nucleic acid molecules are administered in a manner compatible with the dosage formulation, and in such amount as will be effective. In the case of a recombinant nucleic acid encoding a natural binding domain and/or binding partner therefor, such an amount should be sufficient to result in production of a detectable amount of the labeled protein or peptide, as discussed above. In the case of a protein modifying enzyme, the amount produced by expression of a nucleic acid molecule should be sufficient to ensure that at least 10% of natural binding domains or binding partners therefor will undergo modification if they comprise a target site recognized by the enzyme being assayed. Lastly, the amount of a nucleic acid encoding a candidate modulator of a protein modifying enzyme of the invention must be sufficient to ensure production of an amount of the candidate modulator which can, if effective, produce a change of at least 10% in the effect of the target protein modifying enzyme on FRET or other label emission resulting from binding of a natural binding domain to its binding partner or, if administered to a patient, an amount which is prophylactically and/or therapeutically effective.

When the end product (e.g. an antisense RNA molecule or ribozyme) is administered directly, the dosage to be administered is directly proportional to the amount needed per cell and the number of cells to be transfected, with a correction factor for the efficiency of uptake of the molecules. In cases in which a gene must be expressed from the nucleic acid molecules, the strength of the associated transcriptional regulatory sequences also must be considered in calculating the number of nucleic acid molecules per target cell that will result in adequate levels of the encoded product. Suitable dosage ranges are on the order of, where a gene expression construct is administered, 0.5- to 1 µg, or 1–10 µg, or optionally 10–100 µg of nucleic acid in a single dose. It is conceivable that dosages of up to 1 mg may be advantageously used. Note that the number of molar equivalents per cell vary with the size of the construct, and that absolute amounts of DNA used should be adjusted accordingly to ensure adequate gene copy number when large constructs are injected.

If no effect (e.g., of a protein modifying enzyme or an inhibitor thereof) is seen within four orders of magnitude in either direction of the starting dosage, it is likely that a protein modifying enzyme does not recognize the target site of the natural binding domain (and, optionally, its binding partner) according to the invention, or that the candidate modulator thereof is not of use according to the invention. It is critical to note that when high dosages are used, the concentration must be kept below harmful levels, which may be known if an enzyme or candidate modulator is a drug that is approved for clinical use. Such a dosage should be one (or, preferably, two or more) orders of magnitude below the $LD_{50}$ value that is known for a laboratory mammal, and preferably below concentrations that are documented as producing serious, if non-lethal, side effects.

Components of screening assays of the invention may be formulated in a physiologically acceptable diluent such as water, phosphate buffered saline, or saline, and further may include an adjuvant. Adjuvants such as incomplete Freund's adjuvant, aluminum phosphate, aluminum hydroxide, or alum are materials well known in the art. Administration of labeled polypeptides comprising a natural binding domain, sequence, polypeptide or a binding partner therefor, a protein modifying enzyme or a candidate modulator as described herein may be either localized or systemic.

Localized Adminstration

Localized administration of a component of an assay of the invention is preferably by via injection or by means of a drip device, drug pump or drug-saturated solid matrix from which the labeled natural binding domain, sequence or polypeptide, binding partner therefor, modifying enzyme or candidate modulator therefor or nucleic acid encoding any of these can diffuse implanted at the target site. When a tissue that is the target of delivery according to the invention is on a surface of an organism, topical administration of a pharmaceutical composition is possible.

Compositions comprising a composition of—or of use in the invention which are suitable for topical administration can take one of several physical forms, as summarized below:

(i) A liquid, such as a tincture or lotion, which may be applied by pouring, dropping or "painting" (i.e. spreading manually or with a brush or other applicator such as a spatula) or injection.

(ii) An ointment or cream, which may be spread either manually or with a brush or other applicator (e.g. a spatula), or may be extruded through a nozzle or other small opening from a container such as a collapsible tube.

(iii) A dry powder, which may be shaken or sifted onto the target tissue or, alternatively, applied as a nebulized spray.

(iv) A liquid-based aerosol, which may be dispensed from a container selected from the group that comprises pressure-driven spray bottles (such as are activated by squeezing), natural atomizers (or "pump-spray" bottles that work without a compressed propellant) or pressurized canisters.

(v) A carbowax or glycerin preparation, such as a suppository, which may be used for rectal or vaginal administration of a therapeutic composition.

In a specialized instance, the tissue to which a candidate modulator of a protein modifying enzyme is to be delivered for assay (or, if found effective, for therapeutic use) is the lung. In such a case the route of administration is via inhalation, either of a liquid aerosol or of a nebulized powder of. Drug delivery by inhalation, whether for topical or systemic distribution, is well known in the art for the treatment of asthma, bronchitis and anaphylaxis. In particular, it has been demonstrated that it is possible to deliver a protein via aerosol inhalation such that it retains its native activity in vivo (see Hubbard et al., 1989, *J. Clin Invest.*, 84: 1349–1354).

Systemic Administration

Systemic administration of a protein, nucleic acid or other agent according to the invention may be performed by methods of whole-body drug delivery are well known in the art. These include, but are not limited to, intravenous drip or injection, subcutaneous, intramuscular, intraperitoneal, intracranial and spinal injection, ingestion via the oral route, inhalation, trans-epithelial diffusion (such as via a drug-impregnated, adhesive patch) or by the use of an implantable, time-release drug delivery device, which may comprise a reservoir of exogenously-produced protein, nucleic acid or other material or may, instead, comprise cells that produce and secrete a natural binding domain and/or a binding partner therefor, protein modifying enzyme or candidate modulator thereof. Note that injection may be performed either by conventional means (i.e. using a hypodermic needle) or by hypospray (see Clarke and Woodland, 1975, *Rheumatol. Rehabil.*, 14: 47–49). Components of assays of the invention can be given in a single- or multiple dose.

Delivery of a nucleic acid may be performed using a delivery technique selected from the group that includes, but is not limited to, the use of viral vectors and non-viral vectors, such as episomal vectors, artificial chromosomes, liposomes, cationic peptides, tissue-specific cell transfection and transplantation, administration of genes in general vectors with tissue-specific promoters, etc.

F. Kits According to the Invention i. A Kit for Assaying the Activity of a Protein-modifying Enzyme In order to facilitate convenient and widespread use of the invention, a kit is provided which contains the essential components for screening the activity of a an enzyme which mediates a change in protein modification, as described above. A labeled, natural binding domain, sequence or polypeptide, as defined above, and a differentially labeled binding partner which binds it specifically in a modification-dependent manner is provided, as is a suitable reaction buffer for in vitro assay or, alternatively, cells or a cell lysate. A reaction buffer which is "suitable" is one which is permissive of the activity of the enzyme to be assayed and which permits modification dependent binding of the natural binding domain, sequence or polypeptide and the binding partner. The labeled components are provided as peptide/protein or a nucleic acid comprising a gene expression construct encoding the one or more of a peptide/protein, as discussed above. Polypeptides in a kit of the invention are supplied either in solution (preferably refrigerated or frozen) in a buffer which inhibits degradation and maintains biological activity, or are provided in dried form, i.e., lyophilized. In the latter case, the components are resuspended prior to use in the reaction buffer or other biocompatible solution (e.g. water, containing one or more of physiological salts, a weak buffer, such as phophate or Tris, and a stabilizing substance such as glycerol, sucrose or polyethylene glycol); in the latter case, the resuspension buffer should not inhibit modification-dependent protein binding when added to the reaction buffer in an amount necessary to deliver sufficient protein for an assay reaction. Polypeptides provided as nucleic acids are supplied- or resuspended in a buffer which permits either transfection/transformation into a cell or organism or in vitro transcription/translation, as described above. Each of these components is supplied separately contained or in admixture with one or more of the others in a container selected from the group that includes, but is not limited to, a tube, vial, syringe or bottle.

Optionally, the kit includes cells. Eukaryotic or prokaryotic cells, as described above, are supplied in- or on a liquid or solid physiological buffer or culture medium (e.g. in suspension, in a stab culture or on a culture plate, e.g. a Petri dish). For ease of shipping, the cells are typically refrigerated, frozen or lyophilized in a bottle, tube or vial. Methods of cell preservation are widely known in the art; suitable buffers and media are widely known in the art, and are obtained from commerical suppliers (e.g., Gibco/LifeTechnologies) or made by standard methods (see, for example Sambrook et al., 1989, *Molecular Cloning. A Laboratory Manual.*, 2nd Edition, Cold Spring Harbor Laboratory Press, Cold Spring Harbor, N.Y.).

An enzyme being assayed according to the invention is added to the assay system either as a protein (isolated, partially-purified or present in a crude preparation such as a cell extract or even a living cell) or a recombinant nucleic acid. Methods of expressing a nucleic acid comprising an enzyme or other protein are well known in the art (see again above).

An assay of the invention is carried out using the kit according to the methods described above and elsewhere herein.

ii A Kit for Screening Candidate Modulator of Protein-modifying Enzyme Activity

A candidate modulator of post-translational modification may be assayed using a kit of the invention. A kit as described above is used for this application, with the assay performed further comprising the addition of a candidate modulator of the modifying enzyme which is present to the reaction system. Optionally, a protein-modifying enzyme is supplied with the kit, either as a protein or nucleic acid as described above.

Assays of protein activity are performed as described above. At a minimum, three detections are performed, one in which the labeled natural binding domain and its binding partner are present without the modifying enzyme or candidate modulator thereof (control reaction A), one in which the same polypeptide components are incubated with the modifying enzyme under conditions which permit the modification reaction to occur (control reaction B) and one in which the modifying enzyme and candidate inhibitor are both incubated with the labeled natural binding domain and corresponding binding partner under conditions which permit the modification reaction to occur (test reaction). The result of the last detection procedure is compared with those of the first two controls; the candidate inhibitor is judged to be efficacious if there is a shift in either of the observed amount of FRET or the rate at which FRET changes or, alternatively, or another index of fluorescence, such as monomer/excimer fluorescence, fluorescence correlation spectroscopy (FCS) or fluorescence anisotropy of at least 10% away from that observed in control reaction B toward that observed in control reaction A.

Use

The invention is useful in monitoring the activity of a protein-modifying enzyme, whether the protein is isolated, partially-purified, present in a crude preparation or present in a living cell. The invention is further useful in assaying a cell or cell extract for the presence- or level of activity of a protein modifying enzyme. The invention is additionally useful in assaying the activity of naturally-occurring (mutant) or non-natural (engineered) isoforms of known protein modifying enzymes or, instead, that of novel (natural or non-natural) enzymes. The invention is of use in assaying the efficacy of candidate modulators of the activity of a protein modifying enzyme in inhibiting or enhancing the activity of that enzyme; moreover, is useful to screen potential therapeutic drugs for activity against cloned and/or purified enzymes that may have important clinical pathogenicities when mutated. The invention is further of use in the screening of candidate bioactive agents (e.g., drugs) for side effects, whereby the ability of such an agent to modulate the activity of a protein modifying enzyme may be indicative a propensity toward provoking unintended side-effects to a therapeutic or other regimen in which that agent might be employed.

OTHER EMBODIMENTS

Other embodiments will be evident to those of skill in the art. It should be understood that the foregoing description is provided for clarity only and is merely exemplary. The spirit and scope of the present invention are not limited to the above examples, but are encompassed by the following claims.

What is claimed is:

1. A method for monitoring activity of an enzyme comprising performing a detection step to detect binding of an isolated natural binding domain and a binding partner therefor as a result of contacting one or both of said isolated natural binding domain and said binding partner with said enzyme, wherein said isolated natural binding domain includes a site for post-translational modification and binds said binding partner in a manner dependent upon modification of said site by said enzyme and wherein detection of binding of said isolated natural binding domain and said binding partner as a result of said contacting is indicative of enzyme activity, wherein said site for post-translational modification does not include a sequence which directs modification by a protein kinase or phosphatase.

2. A method for monitoring activity of an enzyme comprising performing a detection step to detect dissociation of an isolated natural binding domain and a binding partner therefor as a result of contacting one or both of said isolated natural binding domain and said binding partner with said enzyme, wherein said isolated natural binding domain includes a site for post-translational modification and binds said binding partner in a manner dependent upon modification of said site by said enzyme and wherein detection of dissociation of said isolated natural binding domain and said binding partner as a result of said contacting is indicative of enzyme activity, wherein said site for post-translational modification does not include a sequence which directs modification by a protein kinase or phosphatase.

3. The method of claim 1 or 2, wherein at least one of said isolated natural binding domain and said binding partner is labeled with a detectable label.

4. The method of claim 3, wherein said label emits light.

5. The method of claim 4, wherein said light is fluorescent.

6. The method of claim 5, wherein said detection step is to detect a change in signal emission by said detectable label.

7. The method according to claim 6, wherein said method further comprises exciting said detectable label and monitoring fluorescence emission.

8. The method according to claim 1 or 2, wherein said enzyme is one of the following enzymes: a carbohydrate transferase, a ubiquitin activating enzyme E1, a ubiquitin conjugating enzyme E2, a ubiquitin conjugating enzyme Ubc9, a ubiquitin protein ligase E3, a poly (ADP-ribose) polymerase, a fatty acyl transferase and an NAD:Arginng ADP-ribosyltransferase, and wherein said enzyme is not a kinase or phosphatase.

9. A method for monitoring modulation of the activity of an enzyme comprising contacting an isolated natural binding domain and a binding partner with an agent which modulates the activity of said enzyme, performing a detection step to detect binding of an isolated natural binding domain and a binding partner therefor as a result of contacting one or both of said isolated natural binding domain and said binding partner with said enzyme, wherein said isolated natural binding domain includes a site for post-translational modification by said enzyme and binds to or dissociates from said binding partner in a manner dependent upon modification of said site by said enzyme and wherein detection of binding or dissociation of said isolated natural binding domain and said binding partner as a result of said contacting is indicative of modulation of enzyme activity by said candidate modulator.

* * * * *